US012239826B2

(12) United States Patent
Bom et al.

(10) Patent No.: US 12,239,826 B2
(45) Date of Patent: Mar. 4, 2025

(54) DRUG DELIVERY ASSEMBLY WITH MOVING SENSOR SYSTEM

(71) Applicant: Novo Nordisk A/S, Bagsvaerd (DK)

(72) Inventors: Lars Morten Bom, Hoersholm (DK); Brian Mouridsen, Fredensborg (DK); Jesper Hoeholt, Melby (DK); Bennie Peder Smiszek Pedersen, Haslev (DK); Laurits Hoejgaard Olesen, Koebenhavn K (DK); Kim Ejholm Hansen, Alleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 878 days.

(21) Appl. No.: 17/292,952

(22) PCT Filed: Dec. 3, 2019

(86) PCT No.: PCT/EP2019/083468
§ 371 (c)(1),
(2) Date: May 11, 2021

(87) PCT Pub. No.: WO2020/115031
PCT Pub. Date: Jun. 11, 2020

(65) Prior Publication Data
US 2022/0001110 A1 Jan. 6, 2022

(30) Foreign Application Priority Data
Dec. 4, 2018 (EP) .................................. 18209976

(51) Int. Cl.
*A61M 5/315* (2006.01)
(52) U.S. Cl.
CPC .... *A61M 5/31551* (2013.01); *A61M 5/31585* (2013.01); *A61M 2205/3327* (2013.01); *A61M 2205/50* (2013.01)

(58) Field of Classification Search
CPC .......... A61M 5/31551; A61M 5/31585; A61M 2205/3327; A61M 2205/50
See application file for complete search history.

(56) References Cited

U.S. PATENT DOCUMENTS 6,482,185 B1 11/2002 Hartmann
6,585,698 B1 7/2003 Packman et al.
(Continued)

FOREIGN PATENT DOCUMENTS

CN 106999675 A 8/2017
CN 107750174 A 3/2018
(Continued)

OTHER PUBLICATIONS

ATMEL Datasheet ATtiny 26, 2010, pp. 1-182.
(Continued)

*Primary Examiner* — Dung T Ulsh
(74) *Attorney, Agent, or Firm* — Wesley Nicolas

(57) ABSTRACT

A drug delivery assembly comprising a magnetic indicator and a sensor system is provided. The indicator is arranged to rotate and move axially relative to a housing component and corresponding to a reference axis, the amount of rotation being indicative of the size of an expelled dose amount. The sensor system comprises a sensor component adapted to measure a property of the indicator indicative of a rotational position and/or a rotational movement of the indicator. The sensor component forms part of release assembly adapted to be moved into engagement with a release member to release a set dose, and subsequently to move axially together with indicator.

13 Claims, 25 Drawing Sheets

(56) References Cited

U.S. PATENT DOCUMENTS

| | | |
|---|---|---|
| 7,511,480 B2 | 3/2009 | Steffen |
| 8,529,520 B2 | 9/2013 | Mattias |
| 8,771,233 B2 | 7/2014 | Watanabe et al. |
| 8,882,704 B2 | 11/2014 | Fago et al. |
| 9,022,988 B1 | 5/2015 | Shaban |
| 10,420,895 B2 | 9/2019 | Erbstein et al. |
| 11,083,853 B2 | 8/2021 | Grubbe |
| 11,197,957 B2 | 12/2021 | Kiilerich et al. |
| 2002/0101210 A1 | 8/2002 | Boisvert et al. |
| 2006/0175427 A1 | 8/2006 | Jonientz et al. |
| 2008/0053805 A1 | 3/2008 | Wanek |
| 2009/0318865 A1 | 12/2009 | Moller et al. |
| 2013/0079727 A1 | 3/2013 | Schildt et al. |
| 2014/0243787 A1 | 8/2014 | Mukai et al. |
| 2014/0276583 A1 | 9/2014 | Chen et al. |
| 2015/0352288 A1 | 12/2015 | Andersen |
| 2016/0008546 A1 | 1/2016 | Rekaya et al. |
| 2016/0015903 A1 | 1/2016 | Madsen et al. |
| 2016/0030679 A1 | 2/2016 | Nielsen et al. |
| 2016/0051760 A1 | 2/2016 | Krusell et al. |
| 2017/0274148 A1 | 9/2017 | Mews et al. |
| 2017/0286638 A1 | 10/2017 | Searle et al. |
| 2018/0200452 A1 | 7/2018 | Marcoz et al. |
| 2018/0207366 A1 | 7/2018 | Marcoz et al. |
| 2018/0228979 A1 | 8/2018 | Schildt et al. |
| 2020/0023137 A1 | 1/2020 | Byerly et al. |
| 2020/0230324 A1 | 7/2020 | Pedersen et al. |
| 2020/0238011 A1* | 7/2020 | Veasey .............. A61M 5/31568 |
| 2020/0330693 A1 | 10/2020 | Olesen et al. |
| 2022/0023546 A1 | 1/2022 | Jespersen et al. |

FOREIGN PATENT DOCUMENTS

| | | | |
|---|---|---|---|
| CN | 107835702 | A | 3/2018 |
| CN | 108472454 | A | 8/2018 |
| CN | 113286625 | A | 8/2021 |
| DE | 29904864 | | 8/2000 |
| DE | 102009003721 | A1 | 10/2010 |
| DK | 200100240 | | 11/2001 |
| EP | 1808193 | A1 | 7/2007 |
| EP | 2060284 | A1 | 5/2009 |
| EP | 2692378 | A1 | 2/2014 |
| EP | 2762184 | A1 | 8/2014 |
| EP | 3058970 | A1 | 8/2016 |
| EP | 3103492 | A1 | 12/2016 |
| GB | 2256050 | A | 11/1992 |
| IN | 104981262 | A | 10/2015 |
| JP | 2013228313 | A | 11/2013 |
| WO | 9709080 | A1 | 3/1997 |
| WO | 02064196 | | 8/2002 |
| WO | 03/047426 | | 6/2003 |
| WO | 04078241 | | 9/2004 |
| WO | 2005009231 | A1 | 2/2005 |
| WO | 2005/046559 | A2 | 5/2005 |
| WO | 05/110387 | A2 | 11/2005 |
| WO | 06/045525 | | 5/2006 |
| WO | 2009062675 | A1 | 5/2009 |
| WO | 2019175790 | | 9/2009 |
| WO | 2010005688 | A2 | 1/2010 |
| WO | 2010052275 | A2 | 5/2010 |
| WO | 2010056367 | A1 | 5/2010 |
| WO | 2010070799 | A1 | 6/2010 |
| WO | 2010/098929 | A1 | 9/2010 |
| WO | 2010/098931 | A1 | 9/2010 |
| WO | 2010098927 | A1 | 9/2010 |
| WO | 2010098928 | A1 | 9/2010 |
| WO | 2010112575 | A1 | 10/2010 |
| WO | 2010128493 | A2 | 11/2010 |
| WO | 2010142598 | A1 | 12/2010 |
| WO | 2012046199 | A1 | 4/2012 |
| WO | 2013050535 | A2 | 4/2013 |
| WO | 2014020008 | A1 | 2/2014 |
| WO | 2014037331 | A1 | 3/2014 |
| WO | 2014064691 | A2 | 5/2014 |
| WO | 2014111336 | A1 | 7/2014 |
| WO | 2014161952 | A1 | 10/2014 |
| WO | 2015075136 | | 5/2015 |
| WO | 2016050902 | A1 | 4/2016 |
| WO | 2016142216 | A1 | 9/2016 |
| WO | 2016193229 | A1 | 12/2016 |
| WO | 2016198516 | A1 | 12/2016 |
| WO | 2017013463 | A1 | 1/2017 |
| WO | 2017148855 | A1 | 9/2017 |
| WO | 2018031390 | A1 | 2/2018 |
| WO | 2018138542 | | 8/2018 |
| WO | 2018160425 | A1 | 9/2018 |
| WO | 2019001919 | A1 | 1/2019 |
| WO | 2019057911 | A1 | 3/2019 |
| WO | 2019175615 | | 9/2019 |
| WO | 2020035406 | | 2/2020 |

OTHER PUBLICATIONS

U.S. Appl. No. 13/375,033—Advisory Action dated Jun. 29, 2015.
U.S. Appl. No. 13/375,033—Office Action dated Nov. 7, 2014.
WO2010142598—International Preliminary Report on Patentability, dated Dec. 6, 2011.

* cited by examiner

Fig. 6
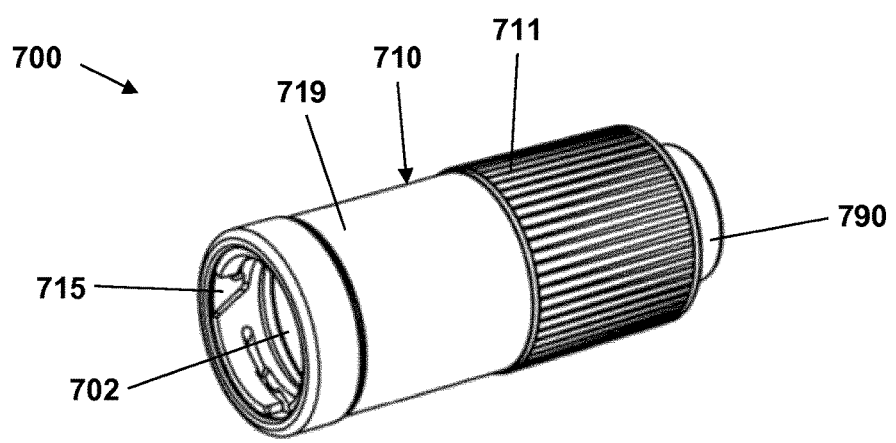
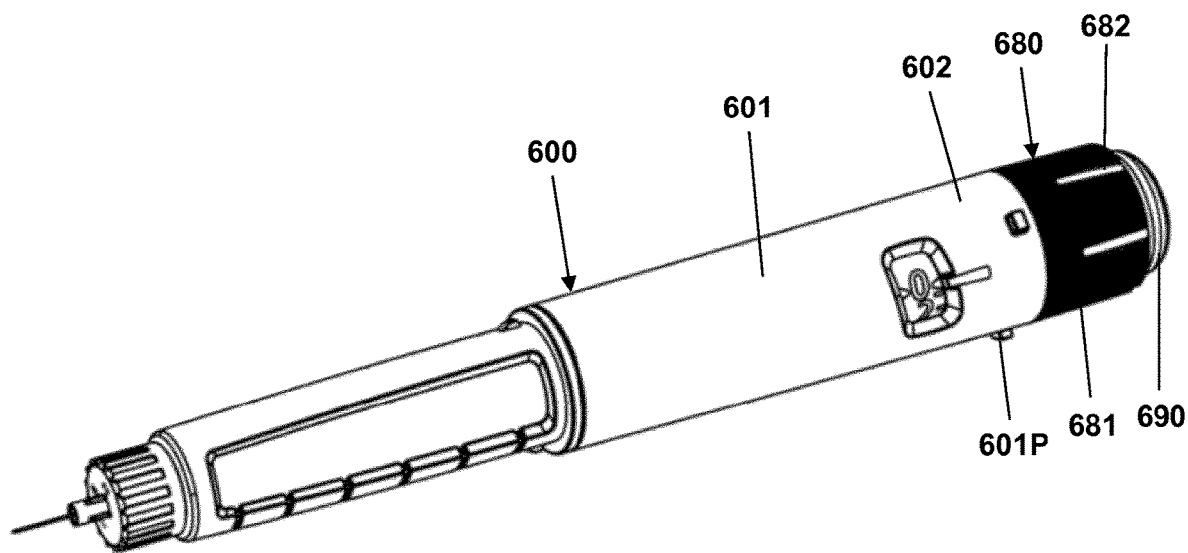

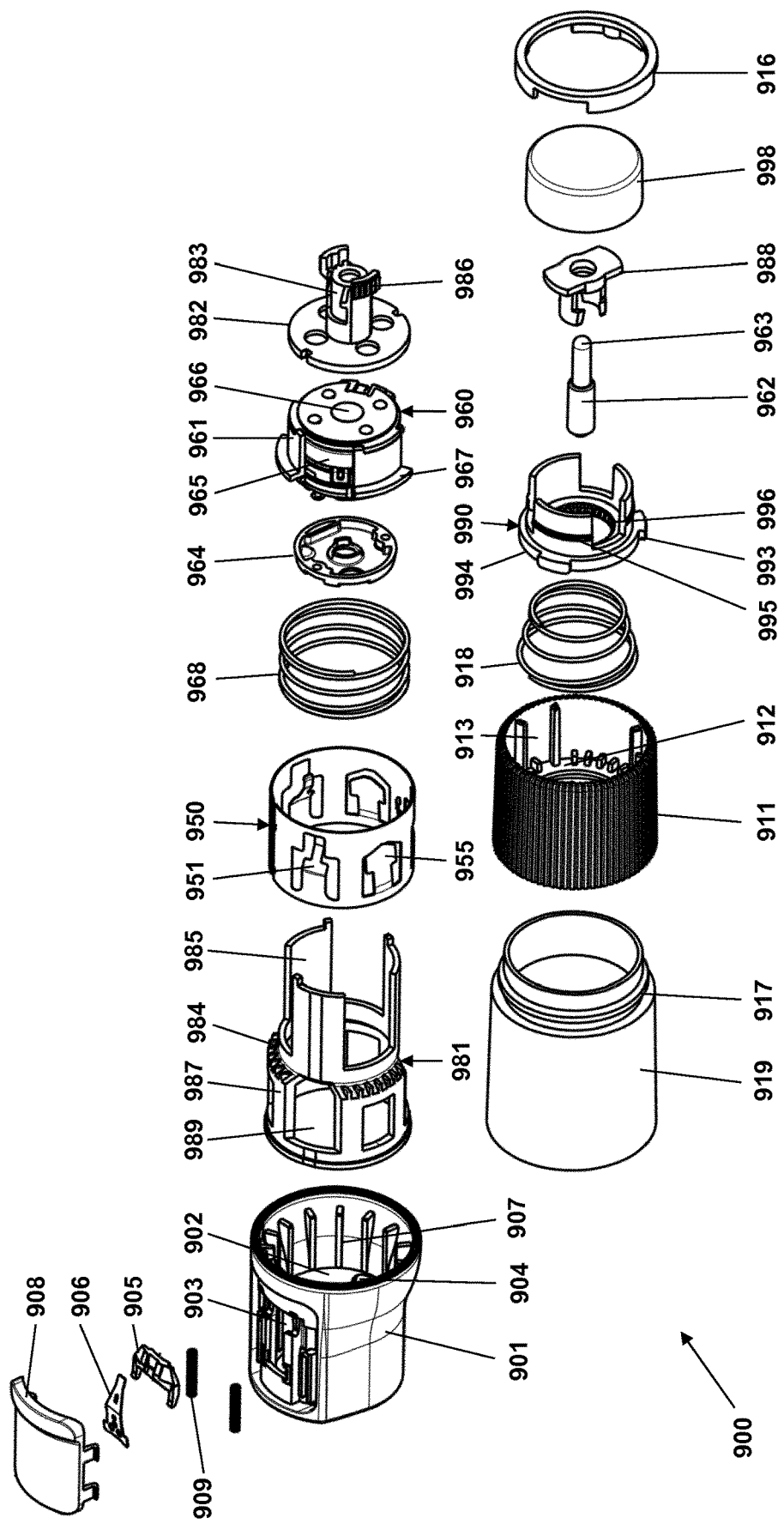

DRUG DELIVERY ASSEMBLY WITH MOVING SENSOR SYSTEM

CROSS-REFERENCE TO RELATED APPLICATIONS

This application is a 35 U.S.C. § 371 National Stage application of International Application PCT/EP2019/083468 (published as WO 2020/115031), filed Dec. 3, 2019, which claims priority to European Patent Application 18209976.2, filed Dec. 4, 2018; the contents of which are incorporated herein by reference.

The present invention generally relates to a drug delivery assembly in which a rotational property of an indicator is being measured, and in which the indicator at the same time is moving axially. In a specific aspect the present invention relates to medical devices for which the generation, collecting and storing of data are relevant. In specific embodiments the invention relates to devices and systems for capturing drug delivery dose data in a reliable and efficient way.

BACKGROUND OF THE INVENTION

In the disclosure of the present invention reference is mostly made to drug delivery devices comprising a threaded piston rod driven by a rotating drive member, such devices being used e.g. in the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be durable devices adapted to be used with prefilled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, and the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of injection information from medication delivery systems.

Some injection devices integrate this monitoring/acquisition mechanism into the device itself, e.g. as disclosed in US 2009/0318865 and WO 2010/052275, however, most devices of today are without it. The most widely used devices are purely mechanical devices being either durable or prefilled. The latter devices are to be discarded after being emptied and so inexpensive that it is not cost-effective to build-in electronic data acquisition functionality in the device itself. Addressing this problem a number of solutions have been proposed which would help a user to generate, collect and distribute data indicative of the use of a given medical device.

For example, WO 2014/037331 describes in a first embodiment an electronic supplementary device (also named "add-on module" or "add-on device") adapted to be releasably attached to a drug delivery device of the pen type. The device includes a camera and is configured to perform optical character recognition (OCR) on captured images from a rotating scale drum visible through a dosage window on the drug delivery device, thereby to determine a dose of medicament that has been dialed into the drug delivery device. WO 2014/037331 also describes a second embodiment of an electronic supplementary device adapted to be releasably attached to a drug delivery device of the pen type comprising a drive screw extending proximally from the device corresponding to a set dose. The supplementary device comprises sensor means for determining axial extension of the drive screw as well as sensor means for detecting operation of the proximal delivery button. WO 2014/020008 discloses an electronic supplementary device adapted to be releasably attached to a drug delivery device of the pen type. The device includes a camera and is configured to determine scale drum values based on OCR. To properly determine the size of an expelled dose the supplementary device further comprises additional electromechanical sensor means to determine whether a dose size is set, corrected or delivered. A further external device for a pen device is shown in WO 2014/161952.

Having regard to the above, it is an object of the present invention to provide devices and methods allowing reliable and efficient operation of a drug delivery assembly comprising sensor means for determining the size of expelled amounts of drug. The sensor means may e.g. be incorporated in a drug delivery device or provided as a user-mountable add-on device. It is a general object of the invention to provide a sensor assembly in which a rotational property of an axially moving indicator can be measured in a reliable and safe way.

DISCLOSURE OF THE INVENTION

In the disclosure of the present invention, embodiments and aspects will be described which will address one or more of the above objects or which will address objects apparent from the below disclosure as well as from the description of exemplary embodiments.

When determining the amount of out-dosed drug from a drug delivery device by measuring rotational movement of an indicator element, e.g. units of insulin, this is done in essentially two different ways: attaching the measuring system so as to move axially with the rotating component or attaching the measuring system non-moveable to the drug delivery device housing.

The present invention is based on the realization that although a given rotating component may be considered to be essentially only rotating, this allowing a stationary measuring system to be used, some rotating components are to a small degree moved axially during operation thereof which may influence accuracy of the measuring system.

Thus, in a first aspect of the invention a drug delivery assembly is provided, comprising a housing, a drug reservoir or means for receiving a drug reservoir, drug expelling means, an actuatable release assembly and a sensor system. The drug expelling means comprises a dose setting member allowing a user to set a dose amount of drug to be expelled from the drug reservoir, a release member actuatable between a proximal position and a distal position, the proximal position allowing a dose amount to be set, the distal position allowing the drug expelling means to expel a set dose, and an indicator adapted to rotate corresponding to a reference axis and relative to the housing during expelling of a dose amount of drug, the amount of rotation being indicative of the size of the expelled dose amount, the indicator being moved axially between a proximal position and a distal position when the release member is moved to its distal position. The actuatable release assembly is moveable between an initial proximal position, an intermediate position in which the release member is engaged in its proximal position, and an actuated distal position in which the release member has been moved to its distal position. The sensor system comprises a sensor component adapted to measure a property of the indicator indicative of a rotational position and/or a rotational movement of the indicator, and a processor configured to determine on the basis of measured values from the sensor component a rotational position and/or amount of rotational movement of the indicator.

As the sensor component is coupled to and moves axially with the release assembly, this allows the sensor component to move axially together with the indicator as the indicator is moved axially between its proximal position and its distal position and thereby to exactly and efficiently determine a rotational position and/or amount of rotational movement of the indicator.

In an exemplary embodiment the drug delivery assembly comprises a drive spring arranged to be strained during dose setting and released by the release member to thereby drive expelling of an amount of drug from the drug reservoir. In such an arrangement the indicator may be actuated to move axially between an initial indicator proximal position, an indicator intermediate position and an actuated indicator distal position, wherein the indicator is adapted to start rotating when in the indicator intermediate position.

In an exemplary embodiment the sensor system is adapted to measure a property of the indicator indicative of rotational position and/or rotational movement of the indicator during axial movement of the indicator between the indicator intermediate position and the actuated indicator distal position, the sensor component moving axially together with the indicator.

A property of the indicator indicative of a first rotational position may be measured with the sensor component axially positioned between the initial proximal and the intermediate position, and a property of the indicator indicative of a second rotational position may be measured with the sensor component axially positioned between the intermediate and the distal position.

The sensor system may comprise a plurality of sensor components, with the processor being configured to determine on the basis of measured values from the plurality of sensor components a rotational position and/or amount of rotational movement of the indicator.

The sensor system may be provided with a switch arranged to be actuated from an off-state to an on-state when the release assembly is actuated from the initial proximal position to the intermediate position to thereby energize the sensor system to an operatable state. The switch, e.g. a mechanical, magnetic or optical switch, may be arranged to be actuated when the release assembly engages the release member in its proximal position. The sensor system may be coupled to and move axially with the release assembly, e.g. in the form of a self-contained electronic module.

In an exemplary embodiment the indicator comprises a magnetic component, with at least one sensor component being a magnet sensor adapted to measure one or more components of a magnetic field.

In a specific embodiment the drug delivery assembly comprises a drug delivery device and an add-on device adapted to be releasably mounted on the drug delivery device. The drug delivery device comprises the housing, the drug reservoir or the means for receiving a drug reservoir, and the drug expelling means. The add-on device comprises the release assembly and the sensor system.

The dose setting member may be rotatable, and the add-on device may further comprise an add-on housing adapted to be releasably attached to the drug delivery device housing, an add-on dose setting member adapted to engage, directly or indirectly, the dose setting member, and an actuatable add-on release member coupled to the release assembly and axially moveable relative to the add-on housing between (i) a proximal dose setting position in which the add-on dose setting member (680, 780), with the add-on device mounted on the drug delivery device, can be operated to rotate the dose setting member to set a dose, and (ii) a distal dose expelling position in which the release member, with the add-on device mounted on the drug delivery device, is moved to its distal position to release a set dose.

The different components of the add-on device and the drug delivery device may be designed as disclosed above for the general assembly.

In a specific aspect of the invention an add-on device per se as described above and adapted to be attached releasably to a drug delivery device of the described type is provided.

In a specific embodiment the add-on device comprises an add-on housing adapted to be releasably attached to the drug delivery device housing, an add-on dose setting member adapted to engage, directly or indirectly, a rotatable device dose setting member, and an actuatable add-on release member coupled to the release assembly and axially moveable relative to the add-on housing between (i) a proximal dose setting position in which the add-on dose setting member (680, 780), with the add-on device mounted on the drug delivery device, can be operated to rotate the dose setting member to set a dose, and (ii) a distal dose expelling position in which the release member, with the add-on device mounted on the drug delivery device, is moved to its distal position to release a set dose.

In a further aspect of the invention a method for capturing dose related data from a drug delivery assembly is provided. The method comprises the steps (i) providing a drug delivery assembly comprising drug expelling means comprising: a dose setting member allowing a user to set a dose amount of drug to be expelled from the drug reservoir, a release member actuatable between a proximal position and a distal position, the proximal position allowing a dose amount to be set, the distal position allowing the drug expelling means to expel a set dose, a drive spring arranged to be strained during dose setting and released by the release member to thereby drive expelling of an amount of drug from the drug reservoir, and an indicator adapted to rotate corresponding to a reference axis and relative to the housing during expelling of a dose amount of drug, the amount of rotation being indicative of the size of the expelled dose amount, the indicator being moved axially between a proximal position and a distal position when the release member is moved to its distal position, an actuatable release assembly moveable between an initial proximal position, an intermediate position in which the release member is engaged in its proximal position, and an actuated distal position in which the release member has been moved to its distal position, and a sensor system comprising a sensor component coupled to and moving axially with the release assembly, the sensor component being adapted to measure a property of the indicator indicative of a rotational position and/or a rotational movement of the indicator, and a processor configured to determine on the basis of measured values from the sensor component a rotational position and/or amount of rotational movement of the indicator. The method comprises the further steps of (ii) moving the release assembly into engagement with the release member, (iii) moving the release assembly to release the drug expelling means to expel a set dose, and (iv) while the indicator is being moved axially by the release assembly after the drug expelling means has been released, operate the sensor system to determine a rotational position and/or amount of rotational movement of the indicator.

In a further more general aspect of the invention a sensor assembly comprising an indicator and a sensor system is provided. The indicator is arranged to rotate and move axially relative to a reference component and corresponding to a reference axis, and the sensor system comprises a sensor component adapted to measure a property of the indicator indicative of a rotational position and/or a rotational movement of the indicator. The sensor component is adapted to move axially together with the indicator. Depending on the type of sensor and the specific design of the sensor system additional sensor components may be incorporated.

By allowing the sensor component to follow the indicator axially as the indicator is translated, the distance between the signal generating indicator can be held constant or the variance in distance can be minimized, the latter depending on the actual design of the assembly and measuring strategy.

In an exemplary embodiment the indicator may be actuated to move axially between an initial proximal and an actuated distal position. Based on measured properties, the sensor system is adapted to determine an initial rotational position of the indicator in the initial axial position, and to determine an actuated rotational position of the indicator in the actuated axial position.

The indicator may be adapted to rotate during actuation, with the sensor system, based on measured properties, being adapted to determine a property related to rotation of the indicator, e.g. the amount of rotation expressed in number of degrees or number of full rotations.

In an exemplary embodiment the indicator can be actuated to move axially between an initial proximal, an intermediate position and an actuated distal position, with the indicator being adapted to start rotating when in the intermediate axial position. In such a set-up the sensor system may be adapted to measure a property of the indicator indicative of rotational movement of the indicator during axial movement of the indicator between the intermediate position and the actuated distal position, the sensor component moving axially together with the indicator, this ensuring that rotational movement of the indicator can be measured and determined under essentially constant condition.

In an exemplary embodiment the sensor component is adapted to move axially between an initial proximal, an intermediate position and an actuated distal position, the sensor component moving axially together with the indicator between the intermediate and the actuated distal position. As appears, in such a set-up the sensor component will only move axially together with the indicator for a portion of the axial travel of the latter. Depending on the set-up all or some of the measurements may be made when the sensor component and the indicator move together. For example, a property of the indicator indicative of rotational movement can be measured by the sensor component during axial movement thereof together with the indicator.

On the other hand, a property of the indicator indicative of a first rotational position may be measured with the sensor component axially positioned between the initial proximal and the intermediate position, and a property of the indicator indicative of a second rotational position is measured with the sensor component axially positioned between the intermediate and the distal position. In this set-up the axial distance between the sensor component and the indicator will vary between the two measurements, however, as the sensor component moves together with the indicator for a portion of the axial travel the difference between the measuring conditions can be reduced. Alternatively, the first rotational position may be determined when or after the sensor component and the indicator start to move axially together, this allowing both rotational positions to be determined under essentially identical measuring conditions.

In an exemplary embodiment the sensor system as such may be adapted to move axially together with the indicator. The indicator may comprise a magnetic component with the sensor component(s) being a magnet sensor adapted to measure one or more components of a magnetic field.

In a further aspect of the invention a drug delivery system comprising a sensor assembly as described above is provided, the drug delivery system comprising a drug delivery device and an add-on device adapted to be releasably mounted on the drug delivery device. The drug delivery device comprises a housing forming the reference component, a drug reservoir or means for receiving a drug reservoir, drug expelling means comprising a rotatable dose setting member allowing a user to set a dose amount of drug to be expelled, a release member actuatable between a proximal position and a distal position, the proximal position allowing a dose amount to be set, the distal position allowing the drug expelling means to expel a set dose, a drive spring arranged to be strained during dose setting and released by the release member to thereby drive expelling of an amount of drug from the drug reservoir, as well as the indicator. The indicator is moved axially between the initial and the actuated axial position when the release member is actuated between the proximal and distal position, the indicator rotating during expelling of the amount of drug. The add-on device comprises the sensor system, wherein the measured properties of the indicator correspond to the rotational positions at the beginning respectively the end of expelling of an amount of drug.

Measured properties of the indicator may further correspond to the amount of rotation between the beginning respectively the end of expelling of an amount of drug, this e.g. allowing the sensor system to determine if the indicator has rotated more than 360 degrees.

The add-on device may be provided with a release structure adapted to axially engage and move the release member between the proximal position and the distal position, the sensor system being coupled to and moving axially with the release structure. Alternatively, a unitary drug delivery device is provided comprising an integrated sensor.

In a further aspect of the invention a drug delivery device comprising a sensor assembly as described above is provided, device comprising a housing forming the reference component, a drug reservoir or means for receiving a drug reservoir, drug expelling means comprising a rotatable dose setting member allowing a user to set a dose amount of drug to be expelled, a release member actuatable between a proximal position and a distal position, the proximal position allowing a dose amount to be set, the distal position allowing the drug expelling means to expel a set dose, a drive spring arranged to be strained during dose setting and released by the release member to thereby drive expelling of an amount of drug from the drug reservoir, the indicator, and the sensor system. The indicator is moved axially between the initial and the actuated axial position when the release member is actuated between the proximal and distal position, the indicator rotating during expelling of the amount of drug, and measured properties of the indicator correspond to the rotational positions at the beginning respectively the end of expelling of an amount of drug.

When in the above description the term "between" is used this includes the end points between which a component or structure is moved, i.e. "between A and B" means that a given event may take place at point A or B. When in the above the term "member" is used, this term also covers an assembly comprising a number of components.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin, however, the described module could also be used to create logs for other types of drug, e.g. growth hormone.

BRIEF DESCRIPTION OF THE DRAWINGS

In the following embodiments of the invention will be described with reference to the drawings, wherein FIG. 6 shows a second embodiment of add-on device in combination with a drug delivery device, FIG. 9 shows in exploded view components of a third embodiment of an add-on device.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Figure 1A:
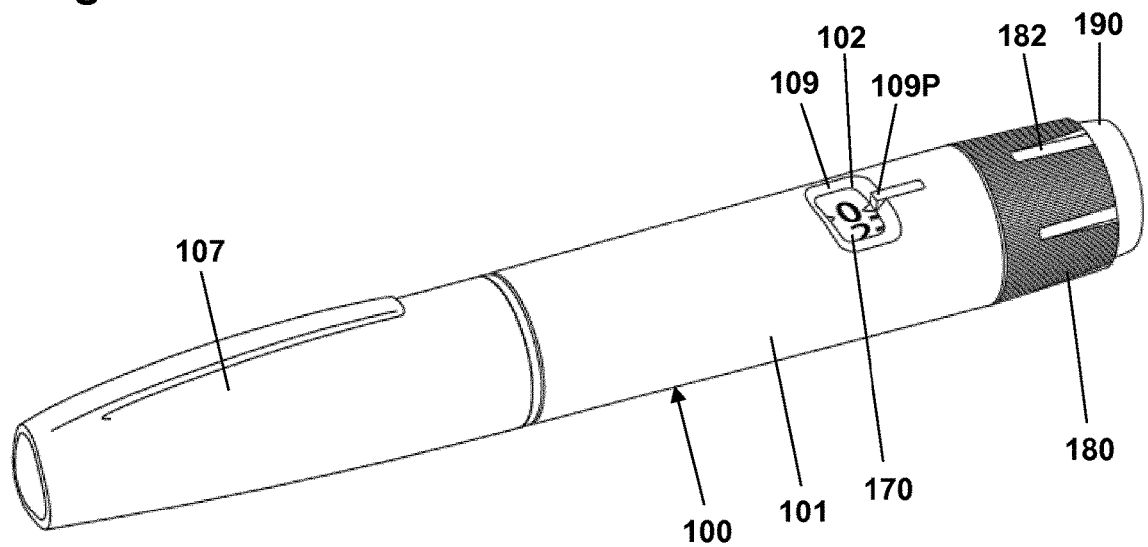
FIG. 1A shows a pen device.

Before turning to embodiments of the present invention per se, an example of a prefilled drug delivery will be described, such a device providing the basis for the exemplary embodiments of the present invention. Although the pen-formed drug delivery device 100 shown in FIGS. 1-3 may represent a "generic" drug delivery device, the actually shown device is a FlexTouch® prefilled drug delivery pen as manufactured and sold by Novo Nordisk A/S, Bagsværd, Denmark.

The pen device 100 comprises a cap part 107 and a main part having a proximal body or drive assembly portion with a housing 101 in which a drug expelling mechanism is arranged or integrated, and a distal cartridge holder portion in which a drug-filled transparent cartridge 113 with a distal needle-penetrable septum is arranged and retained in place by a non-removable cartridge holder attached to the proximal portion, the cartridge holder having openings allowing a portion of the cartridge to be inspected as well as distal coupling means 115 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose setting member 180 with a number of axially oriented grooves 182 serves to manually set a desired dose of drug shown in display window 102 and which can then be expelled when the button 190 is actuated. As will be apparent from the below description, the shown axially oriented grooves 182 may be termed "drive grooves". The dose setting member 180 has a generally cylindrical outer surface 181 (i.e. the dose setting member may be slightly tapered) which in the shown embodiment is textured by comprising a plurality of axially oriented fine grooves to improve finger grip during dose setting. The window is in the form of an opening in the housing surrounded by a chamfered edge portion 109 and a dose pointer 109P, the window allowing a portion of a helically rotatable indicator member 170 (scale drum) to be observed. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose, e.g. as in a FlexPen® manufactured and sold by Novo Nordisk A/S.

Figure 1B:
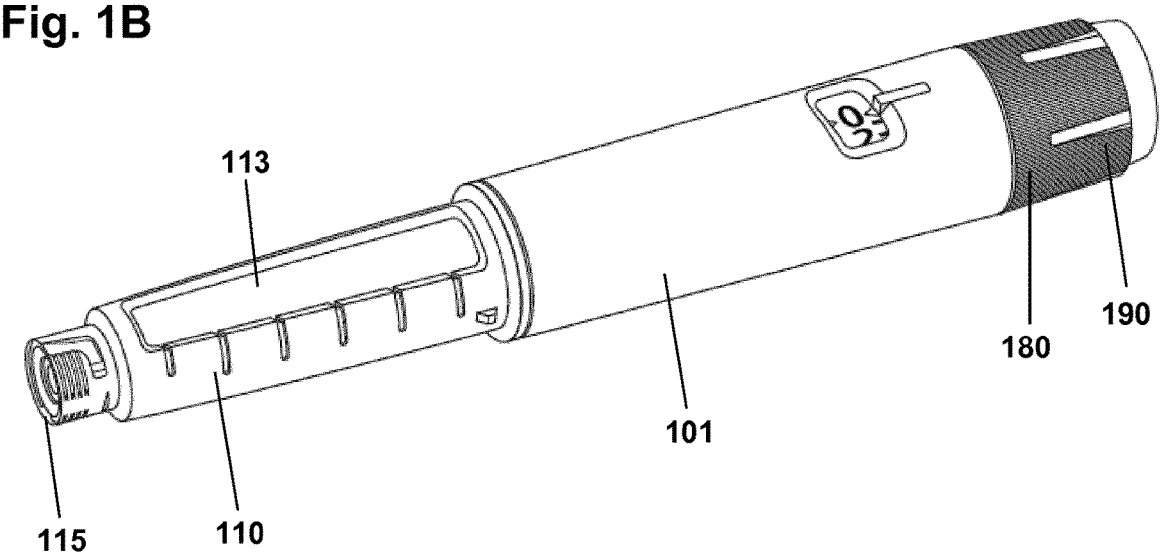
FIG. 1B shows the pen device of FIG. 1A with the pen cap removed.

Although FIG. 1 shows a drug delivery device of the prefilled type, i.e. it is supplied with a premounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

As the invention relates to electronic circuitry adapted to interact with a drug delivery device, an exemplary embodiment of such a device will be described for better understanding of the invention.

Figure 2:
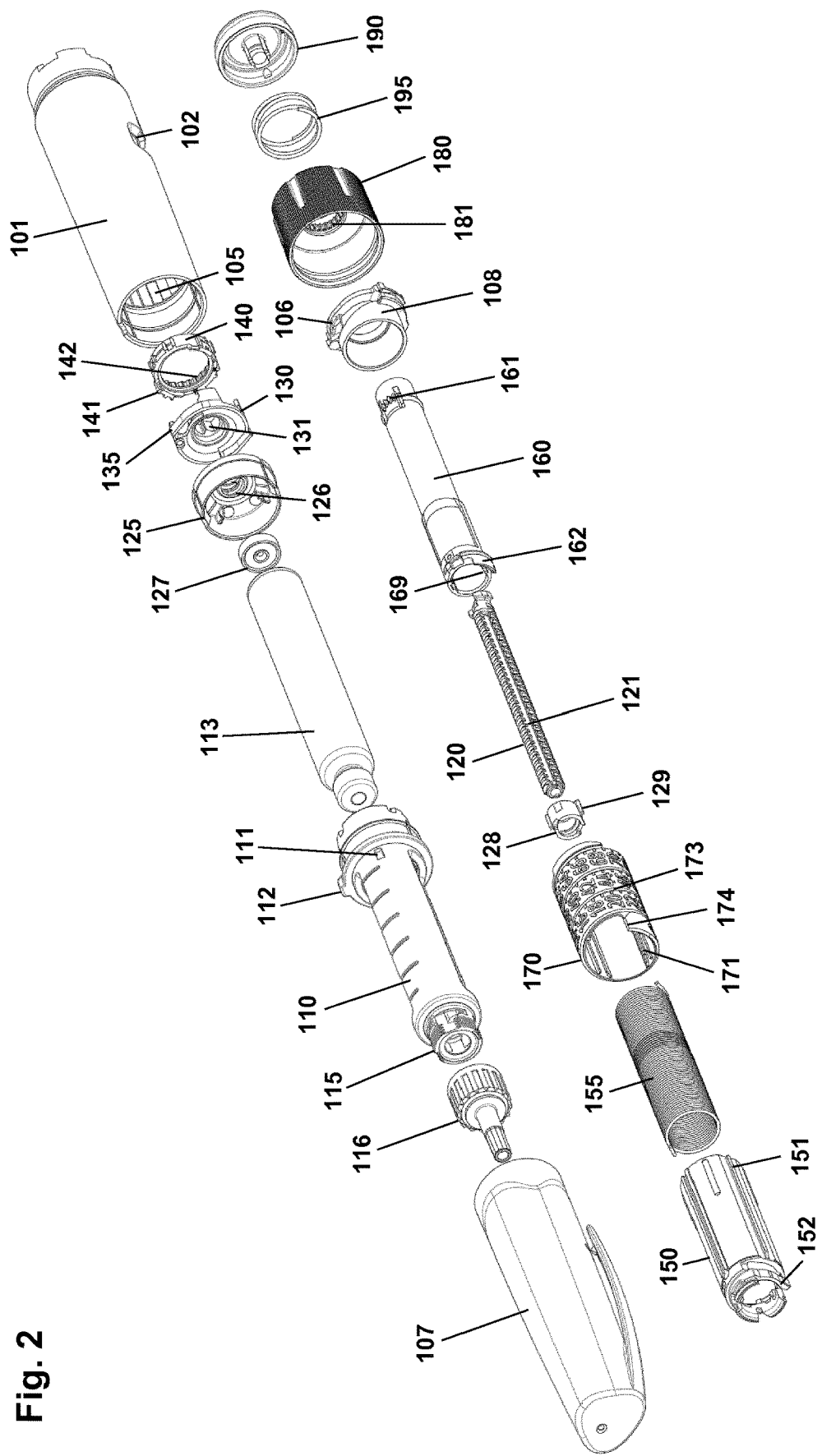
FIG. 2 shows in an exploded view the components of the pen device of FIG. 1A, FIGS. 3A and 3B show in sectional views an expelling mechanism in two states.

FIG. 2 shows an exploded view of the pen-formed drug delivery device 100 shown in FIG. 1. More specifically, the pen comprises a tubular housing 101 with a window opening 102 and onto which a cartridge holder 110 is fixedly mounted, a drug-filled cartridge 113 being arranged in the cartridge holder. The cartridge holder is provided with distal coupling means 115 allowing a needle assembly 116 to be releasably mounted, proximal coupling means in the form of two opposed protrusions 111 allowing a cap 107 to be releasable mounted covering the cartridge holder and a mounted needle assembly, as well as a protrusion 112 preventing the pen from rolling on e.g. a table top. In the housing distal end a nut element 125 is fixedly mounted, the nut element comprising a central threaded bore 126, and in the housing proximal end a spring base member 108 with a central opening is fixedly mounted. A drive system comprises a threaded piston rod 120 having two opposed longitudinal grooves and being received in the nut element threaded bore, a ring-formed piston rod drive element 130 rotationally arranged in the housing, and a ring-formed clutch element 140 which is in rotational engagement with the drive element (see below), the engagement allowing axial movement of the clutch element.

The clutch element is provided with outer spline elements 141 adapted to engage corresponding splines 104 (see FIG. 3B) on the housing inner surface, this allowing the clutch element to be moved between a rotationally locked proximal position, in which the splines are in engagement, and a rotationally free distal position in which the splines are out of engagement. As just mentioned, in both positions the clutch element is rotationally locked to the drive element. The drive element comprises a central bore with two opposed protrusions 131 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 135 adapted to engage corresponding ratchet teeth 105 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 3A and 3B.

On the piston rod an end-of-content (EOC) member 128 is threadedly mounted and on the distal end a washer 127 is rotationally mounted. The EOC member comprises a pair of opposed radial projections 129 for engagement with the reset tube (see below).

The dial system comprises a ratchet tube 150, a reset tube 160, a scale drum 170 with an outer helically arranged pattern forming a row of dose indicia, a user-operated dial member 180 for setting a dose of drug to be expelled, a release button 190 and a torque drive spring 155 (see FIG. 3). The dial member is provided with a circumferential inner teeth structure 181 engaging a number of corresponding outer teeth 161 arranged on the reset tube, this providing a dial coupling which is in an engaged state when the reset tube is in a proximal position during dose setting and in a disengaged state when the reset tube is moved distally during expelling of a dose. The reset tube is mounted axially locked inside the ratchet tube but is allowed to rotate a few degrees (see below). The reset tube comprises on its inner surface two opposed longitudinal grooves 169 adapted to engage the radial projections 129 of the EOC member, whereby the EOC can be rotated by the reset tube but is allowed to move axially. The clutch element is mounted axially locked on the outer distal end portion of the ratchet tube 150, this providing that the ratchet tube can be moved axially in and out of rotational engagement with the housing via the clutch element. The dial member 180 is mounted axially locked but rotationally free on the housing proximal end, the dial ring being under normal operation rotationally locked to the reset tube (see below), whereby rotation of the dial ring results in a corresponding rotation of the reset tube 160 and thereby the ratchet tube. The release button 190 is axially locked to the reset tube but is free to rotate. A return spring 195 provides a proximally directed force on the button and the thereto mounted reset tube. The scale drum 170 is arranged in the circumferential space between the ratchet tube and the housing, the drum being rotationally locked to the ratchet tube via cooperating longitudinal splines 151, 171 and being in rotational threaded engagement with the inner surface of the housing via cooperating thread structures 103, 173, whereby the row of numerals passes the window opening 102 in the housing when the drum is rotated relative to the housing by the ratchet tube. The torque spring is arranged in the circumferential space between the ratchet tube and the reset tube and is at its proximal end secured to the spring base member 108 and at its distal end to the ratchet tube, whereby the spring is strained when the ratchet tube is rotated relative to the housing by rotation of the dial member. A ratchet mechanism with a flexible ratchet arm 152 is provided between the ratchet tube and the clutch element, the latter being provided with an inner circumferential teeth structures 142, each tooth providing a ratchet stop such that the ratchet tube is held in the position to which it is rotated by a user via the reset tube when a dose is set. In order to allow a set dose to be reduced a ratchet release mechanism 162 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Figure 3A:
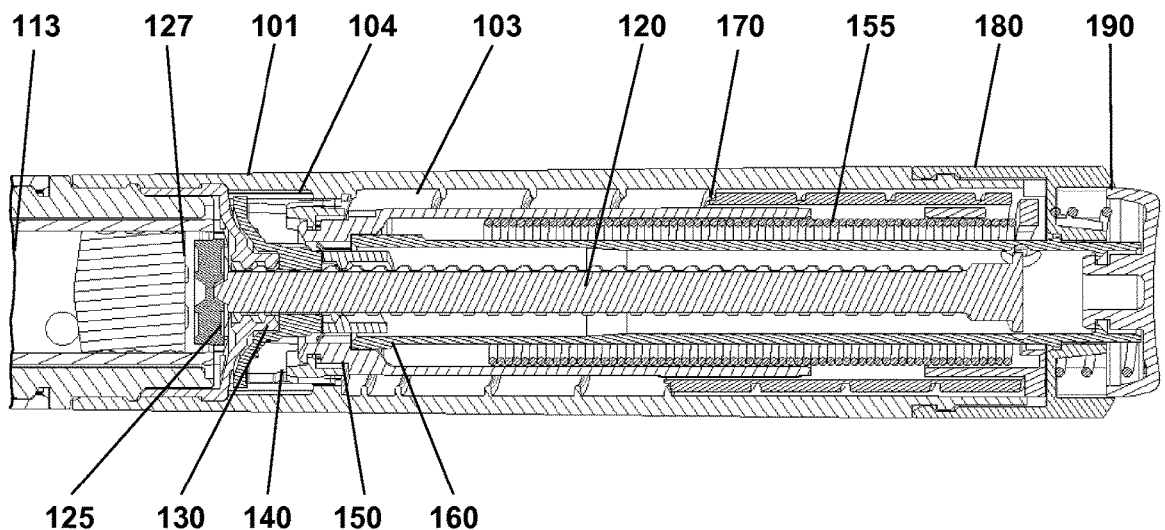

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and the torsion spring is loaded. The dose mechanism is locked to the housing and cannot move. When the push button is pushed down, the dose mechanism is released from the housing and due to the engagement to the dial system the torsion spring will now rotate back the dial system to the starting point and rotate the dose system along with it.

The central part of the dose mechanism is the piston rod 120, the actual displacement of the piston being performed by the piston rod. During dose delivery, the piston rod is rotated by the drive element 130 and due to the threaded interaction with the nut element 125 which is fixed to the housing, the piston rod moves forward in the distal direction. Between the rubber piston and the piston rod, the piston washer 127 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 134 which prevent the drive element from rotating clockwise (seen from the push button end). Due to the engagement with the drive element, the piston rod can thus only move forwards. During dose delivery, the drive element rotates anti-clockwise and the ratchet arms 135 provide the user with small clicks due to the engagement with the ratchet teeth 105, e.g. one click per unit of insulin expelled.

Turning to the dial system, the dose is set and reset by turning the dial member 180. When turning the dial, the reset tube 160, the EOC member 128, the ratchet tube 150 and the scale drum 170 all turn with it due to the dial coupling being in the engaged state. As the ratchet tube is connected to the distal end of the torque drive spring 155, the spring is loaded. During dose setting, the arm 152 of the ratchet performs a dial click for each unit dialed due to the interaction with the inner teeth structure 142 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 102.

The ratchet 152, 142 between the ratchet tube and the clutch element 140 prevents the spring from turning back the parts. During resetting, the reset tube moves the ratchet arm 152, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 142 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

Figure 3B:
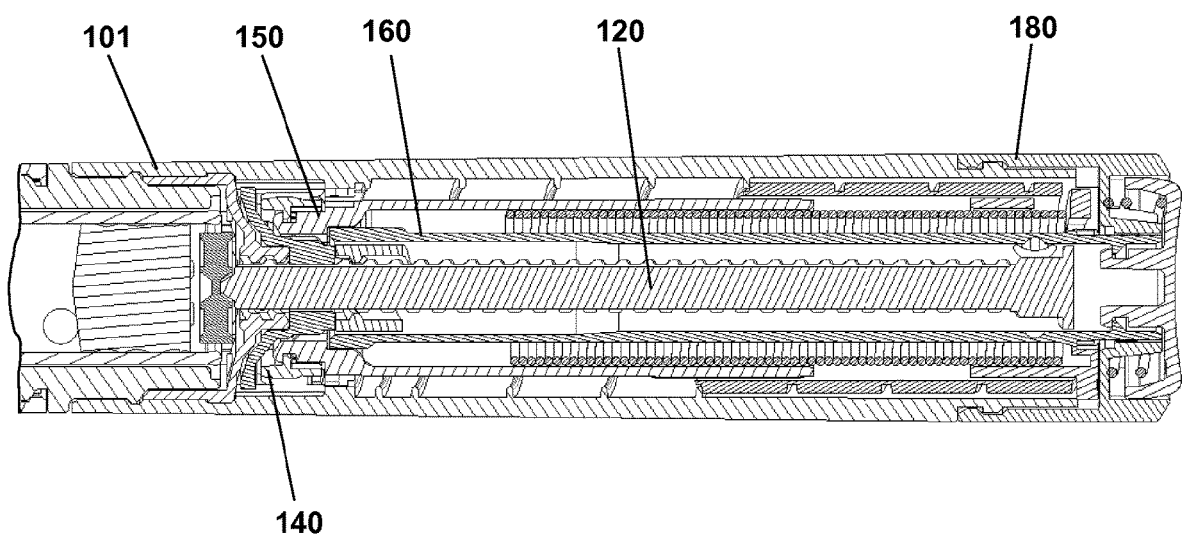

To deliver a set dose, the push button 190 is pushed in the distal direction by the user as shown in FIG. 3B. The dial coupling 161, 181 disengages and the reset tube 160 decouples from the dial member and subsequently the clutch element 140 disengages the housing splines 104. Now the dial mechanism returns to "zero" together with the drive element 130, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 128 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 170 is provided with a distal stop surface 174 adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism.

To prevent accidental over-dosage in case something should fail in the dialing mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 106 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dial member. This feature is provided by the interface between the dial member and the reset tube which as described above are rotationally locked to each other. More specifically, the dial member is provided with circumferential inner teeth structure 181 engaging a number of corresponding outer teeth 161, the latter being arranged on a flexible carrier portion of the reset tube. The reset tube teeth are designed to transmit a torque of a given specified maximum size, e.g. 150-300 Nmm, above which the flexible carrier portion and the teeth will bend inwards and make the dial member turn without rotating the rest of the dial mechanism. Thus, the mechanism inside the pen cannot be stressed at a higher load than the torque limiter transmits through the teeth.

Having described the working principles of a mechanical drug delivery device, embodiments of the present invention will be described.

Figure 4A:
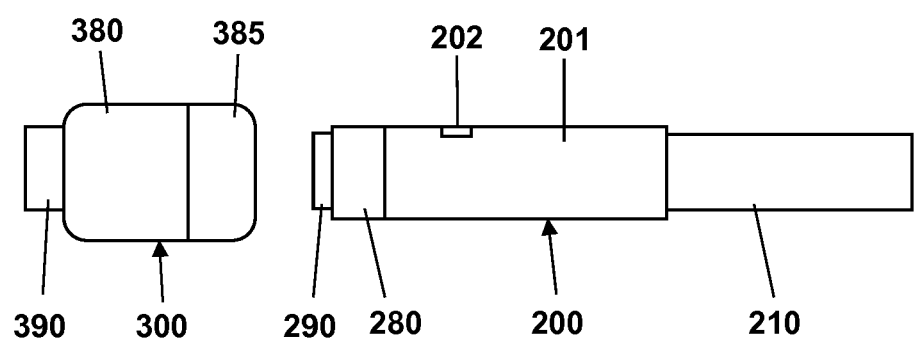
FIGS. 4A and 4B show a schematic representation of an add-on device and a drug delivery device.
Figure 4B:
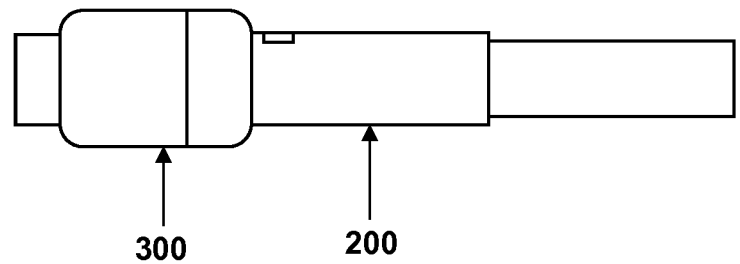

FIGS. 4A and 4B show a schematic representation of a first assembly of a pre-filled pen-formed drug delivery device 200 and a therefor adapted add-on dose logging device 300. The add-on device is adapted to be mounted on the proximal end portion of the pen device housing and is provided with dose setting and dose release means 380 covering the corresponding means on the pen device in a mounted state as shown in FIG. 4B. In the shown embodiment the add-on device comprises a coupling portion 385 adapted to be mounted axially and rotationally locked on the drug delivery housing. The add-on device comprises a rotatable dose setting member 380 which during dose setting is directly or indirectly coupled to the pen dose setting member 280 such that rotational movement of the add-on dose setting member in either direction is transferred to the pen dose setting member. In order to reduce influences from the outside during dose expelling and dose size determination, the outer add-on dose setting member 380 may be rotationally decoupled from the pen dose setting member 280 during dose expelling as will be described in greater detail with reference to the FIG. 5 embodiment. The add-on device further comprises a dose release member 390 which can be moved distally to thereby actuate the pen release member 290. As will be described in greater detail below with reference to FIG. 5 the add-on dose setting member gripped and rotated by the user may be attached directly to the pen housing in rotational engagement therewith.

Alternatively, the shown configuration may be adapted to serve primarily as an aid for people with impaired dexterity to set and release a dose of drug and thus dispense with any dose sensing and dose logging functionality. For such a configuration it is less important that the outer add-on dose setting member is rotationally decoupled from the pen dose setting member 280 during expelling of a dose. Correspondingly, the outer add-on dose setting member may be in permanent rotational engagement with the pen dose setting member 280.

Figure 5:
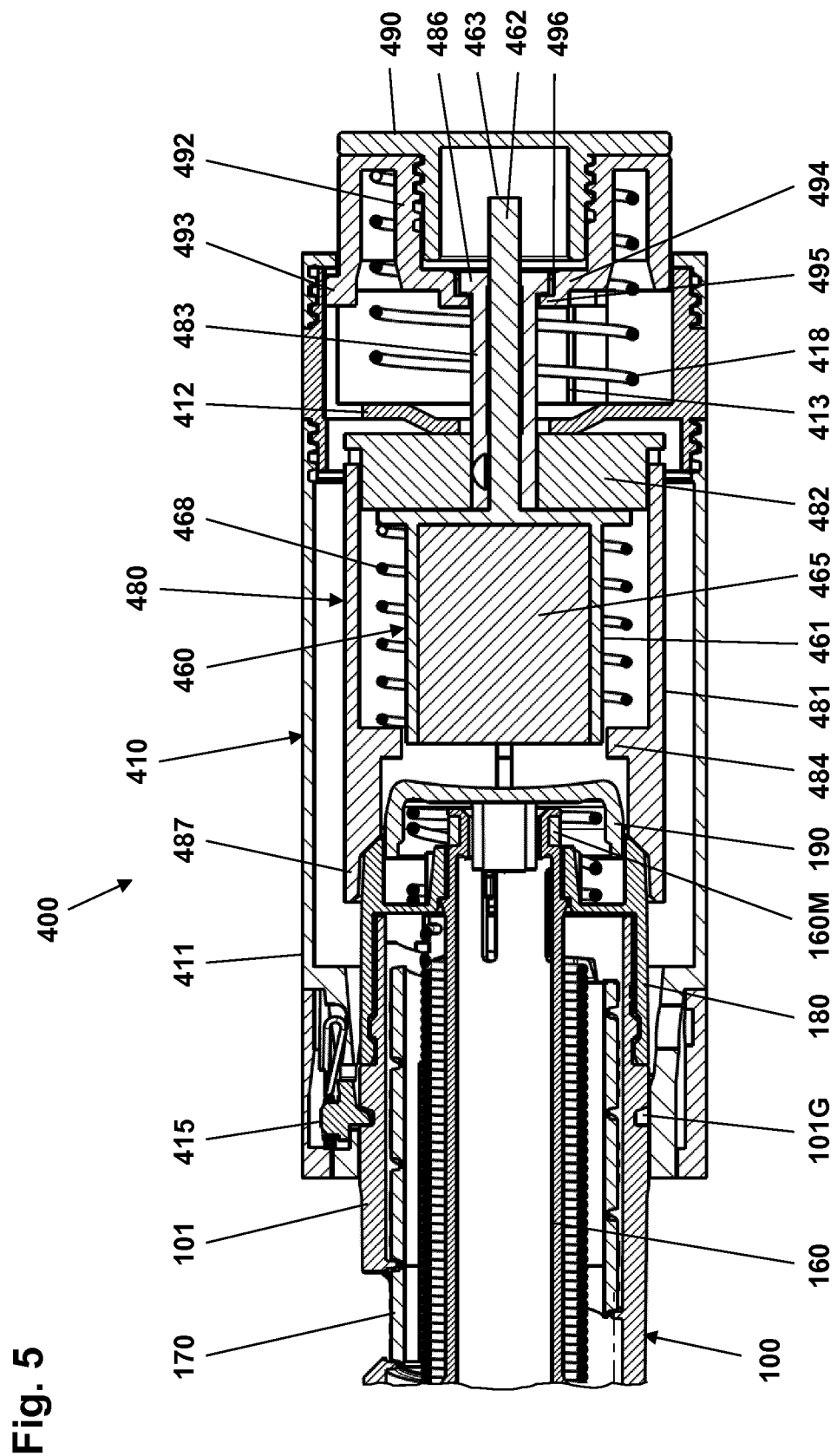
FIG. 5 shows in a cross-sectional view an add-on device mounted on the housing of a drug delivery device.

Turning to FIG. 5 a first exemplary embodiment of an add-on dose logging device 400 adapted to be mounted on a pen-formed drug delivery device 100 will be described in greater detail. The drug delivery device essentially corresponds to the drug delivery device described with reference to FIGS. 1-3 and thus comprises a housing 101, a rotatable dose setting member 180 allowing a user to set a dose amount of drug to be expelled, a release member 190 actuatable between a proximal dose setting position and a distal dose release position, a scale drum 170 as well as a reset tube 160. In order to cooperate with the add-on logging device the drug delivery device has been modified to comprise a generally ring-formed tracer magnet 160M attached to or formed integrally with the reset tube proximal end, the magnet serving as an indicator rotating during expelling of a dose amount, the amount of rotational movement being indicative of the size of the expelled dose amount. Further, the housing has been provided with a circumferential groove 101G just distally of the dose setting member serving as a coupling means for the add-on device.

The add-on device comprises an outer assembly 410 releasably attachable to the drug delivery device housing as well as an inner assembly 480. The inner and outer assemblies are rotationally locked to each other during dose setting, but rotationally de-coupled from each other during dose expelling. The shown embodiment is based on an experimental prototype for which reason some of the structures are formed from a number of assembled parts.

The outer assembly 410 comprises a generally cylindrical housing member 411 defining a general axis for the add-on device and serving as an add-on dose setting member, distally arranged coupling means 415 adapted to engage the coupling groove 101G of the pen housing, and a proximally arranged dose release member 490 coupled to the housing member 411 and axially moveable between an initial proximal position and an actuated distal position. In the shown embodiment the coupling means 415 is in the form of a number of spring-biased coupling members adapted to be releasable received in the housing groove 101G by snap action when the add-on device is slid over the proximal end of the drug delivery device 100, the coupling means thereby axially locking the add-on device to the pen device. The coupling means may be released by e.g. a pulling action or by actuation of a release mechanism. The housing comprises in the proximal portion an inner circumferential flange 412 and a number of axially oriented guide grooves 413. The dose release member 490 comprises a number of peripherally arranged axially oriented flanges 493 received in the guide grooves 413, the grooves providing a proximal stop against which the dose release member is biased by a first return spring 418 supported between the housing flange 412 and the dose release member 490. The dose release member comprises an inner cylindrical skirt portion 492 with a distal inner flange portion 494, the inner flange portion comprising a distal circumferential lip 495 and a proximal array of axially oriented locking splines 496.

The inner assembly 480 comprises an inner housing 481 and a therein arranged axially moveable sensor system in the form of a sensor module 460. The inner housing comprises a proximal wall portion 482 from which a hollow transmission tube 483 extends proximally, an inner circumferential flange portion 484 serving as support for a second biasing spring 468, and a distally extending circumferential skirt portion 487 provided with a number of axially oriented inner projections adapted to be received in the pen dose setting member drive grooves 182 (see FIG. 1A) to thereby rotationally lock the two members to each other, the engagement allowing some axial play during mounting and operation of the add-on device. Alternatively, the skirt portion 487 may be provided with radially inwardly biased drive structures of the type described below. The hollow tube 483 comprises at the proximal end a disc-formed portion having a distally facing stop surface adapted to engage the circumferential lip 495 and a circumferential array of axially oriented splines 486 adapted to engage the locking splines 496 on the dose release member 490 to thereby rotationally lock the inner assembly to the dose release member and thus the outer assembly.

The sensor module 460 comprises a sensor portion and a proximally extending actuation rod portion 462. The sensor portion comprises a generally cylindrical sensor housing 461 in which the electronic circuitry 465 is arranged (shown schematically in FIG. 5). The sensor housing comprises a distal actuation surface adapted to engage the pen actuation member 190. In the initial dose setting mode (i.e. with the dose release member 490 in the initial proximal position) the sensor housing is biased proximally by the second bias spring 468 into engagement with the inner housing proximal wall portion 482 and with the actuation rod 462 extending from the transmission tube 483 into the interior of the dose release member 490, an axial gap being formed between the proximal end 463 of the actuation rod and an inner actuation surface of the dose release member.

The electronic circuitry 465 comprises electronic components including processors means, one or more sensors, one or more switches, wireless transmitter/receiver means and an energy source. The sensors comprise one or more magnetometers adapted to measure a magnetic field generated by the pen tracer magnet 160M, this allowing rotational movement of the pen reset tube and thus the size of an expelled dose to be determined, see e.g. WO 2014/161952. Further sensor means may be provided allowing the type of the device to be recognized, e.g. a light emitter and a colour sensor adapted to determine the colour of the pen release member, the colour serving as an identifier for the drug type contained in the prefilled pen device. The processor means may be in the form of a generic microprocessor or an ASIC, non-volatile program memory such as a ROM providing storage for embedded program code, writable memory such as flash memory and/or RAM for data, and a controller for the transmitter/receiver.

In a situation of use with the add-on device 400 mounted on the pen drug delivery device 100 as shown in FIG. 5, the user starts setting a desired dose by rotating the housing member 411 (i.e. the add-on dose setting member) and with that also the dose release member 490. During dose setting the dose release member is biased towards its initial proximal position whereby it is rotationally locked to the inner assembly 480 via the locking splines 486, 496, this allowing the rotational movement of the add-on dose setting member to be transferred to the inner housing 461 and thus the pen dose setting member 180.

When a dose has been set the user will actuate the dose release member 490 by moving it distally against the force of the first bias spring 418. During the initial release movement the locking splines 486, 496 will disengage, this rotationally de-coupling the inner assembly 480 from the dose release member and thus from the add-on dose setting housing member 411. During the further release movement the dose release member 490 engages the actuation rod proximal end 463 whereby the sensor module 460 during the further release movement will be moved distally towards the pen dose release member 190 and subsequently into contact with the pen release member. The engaging surfaces of the actuation rod 462 and the add-on dose release member 490 are optimized for minimal transfer of rotational movement. Finally, further distal movement of the add-on release member 490 will result in actuation of the pen release member 190 and thereby expelling of the set dose, the sensor module 460 thereby serving as an actuator.

In order to determine the size of an expelled dose the amount of rotation of the tracer magnet 160M and thus the reset tube 160 is determined. More specifically, initial movement of the sensor module will activate a sensor switch (not shown) which in turn will activate the sensor electronics 465 and start sampling of data from the magnetometers, this allowing a rotational start position of the tracer magnet 160M to be determined prior to release of the expelling mechanism. During this period also the colour of the pen release member and thus the type of drug contained in the cartridge may be determined. As the reset tube may rotate more than 360 degrees during expelling of a dose of drug, rotational movement during expelling will be detected and the number of full rotations (if any) determined. When it is detected that rotation of the reset tube has stopped, e.g. when a set dose has been fully expelled or when out-dosing is paused by the user, a rotational end position will be determined, this allowing the size of an expelled dose to be determined. Alternatively, the rotational end position may be determined when the sensor switch detects that the sensor module 460 has returned to its initial position.

As appears, due to the rotational un-coupling of the inner assembly 460 from the outer assembly 480 during drug expelling, it is prevented to a high degree that movements of the outer parts of the add-on device will negatively influence the precise determination of rotational movement and rotational positions of the reset tube 160.

The determined dose size (or data on basis of which a dose size can subsequently be calculated) will be stored together with a time stamp and, if detected, a drug type identifier in a log memory. The content of the log memory may then be transmitted by NFC, Bluetooth® or other wireless means to an external device, e.g. a smartphone, which has been paired with the add-on logging device. An example of a suitable pairing process is described in EP application 17178059.6 which is hereby incorporated by reference.

Turning to FIG. 6 a second exemplary embodiment of an add-on dose logging device 700 adapted to be mounted on a pen-formed drug delivery device 600 will be described in greater detail. The drug delivery device essentially corresponds to the drug delivery devices described with reference to FIGS. 1-3 and thus comprises a housing 601, a rotatable dose setting member 680 allowing a user to set a dose amount of drug to be expelled, a release member 690 actuatable between a proximal dose setting position and a distal dose release position, a scale drum 670 as well as a reset tube 660. In order to cooperate with the add-on logging device 700 the drug delivery device has been modified to comprise a generally ring-formed magnet 660M attached to or formed integrally with the reset tube proximal end, the magnet serving as an indicator rotating during expelling of a dose amount, the amount of rotational movement being indicative of the size of the expelled dose amount. Further, the housing proximal portion 602 has been provided with a number of protuberances 601P just distally of the dose setting member serving as a coupling means for the add-on device. In the shown embodiment three coupling protrusions are located equidistantly on the housing.

The add-on device 700 comprises an outer assembly 710 releasably attachable to the drug delivery device housing as well as an inner assembly (see below). The outer assembly 710 comprises a generally cylindrical distal coupling portion 719 (as in the embodiment of FIG. 4A) defining a general axis for the add-on device, the coupling portion having a generally cylindrical bore 702 adapted to receive a corresponding generally cylindrical coupling portion of the drug delivery pen and being adapted to be mounted axially and rotationally locked on the drug delivery housing by means of a number of bayonet coupling structures 715 adapted to engage the corresponding coupling protuberances 601P on the pen housing and releasably snap into engagement. The add-on device further comprises a proximal dose setting member 711 mounted freely rotatable on the coupling portion and which like in the embodiment of FIG. 5 is coupled to the pen dose setting member 680 such that rotational movement of the add-on dose setting member 711 in either direction is transferred to the pen dose setting member. The add-on device further comprises a dose release member 790 which during dose setting rotates with the dose setting member. A first biasing spring 718 supported on an inner circumferential flange 712 on the dose setting member provides a proximally directed biasing force on the dose release member. As in the embodiment of FIG. 5 the inner and outer assemblies are rotationally locked to each other during dose setting, but rotationally de-coupled from each other during dose expelling.

The inner assembly 780 generally corresponds to the inner assembly 480 of the FIG. 5 embodiments and thus generally comprises the same structures providing the same functionality. Correspondingly, the inner assembly comprises (see FIG. 7A) an inner housing 781 and a therein arranged axially moveable sensor module 760. The inner housing comprises a proximal wall portion 782 from which a hollow transmission tube structure 783 extends proximally, a distal inner circumferential flange portion 784 serving as support for a second biasing spring 768, and a distally extending circumferential skirt portion 787 adapted to engage the pen dose setting member drive grooves 682 (see FIG. 6) to thereby rotationally lock the two members to each other, the engagement allowing some axial play during mounting and operation of the add-on device. In the shown embodiment the structures engaging the dose setting member drive grooves 682 are in the form of flexible fingers 751 allowing for ease of mounting as will be described in greater detail below. The fingers may as shown be mounted to the skirt portion 787, e.g. formed as part of a sheet metal member, or they may be formed integrally with the skirt portion. The hollow tube 783 comprises at the proximal end a number of flange portions 788 having distally facing stop surfaces adapted to engage a circumferential inner flange 795 of the dose release member 790, as well as a number of axially oriented splines adapted to engage the locking splines 796 on the dose release member 790 to thereby rotationally lock the inner assembly to the dose release member and thus the outer assembly.

The sensor module 760 comprises a sensor portion and a proximally extending actuation rod portion 762. The sensor portion comprises a generally cylindrical sensor housing 761 in which the electronic circuitry 765 (see below) is arranged. The sensor housing comprises a distal spacer cap 764 covering the magnet sensors and being adapted to engage the pen actuation member 690. In the initial dose setting mode (i.e. with the dose release member 790 in the initial proximal position) the sensor housing is biased proximally by the second bias spring 768 into engagement with the inner housing proximal wall portion 782 and with the actuation rod 762 extending from the transmission tube 783 into the interior of the dose release member 790, an axial gap being formed between the proximal end 763 of the actuation rod and an inner actuation surface of the dose release member.

The electronic circuitry 765 comprises electronic components including processor means, sensors, an activation switch, e.g. a dome switch actuated by an axial force exerted on the actuation rod portion 762, wireless transmitter/receiver means and an energy source. More specifically, in the shown embodiment the electronic circuitry 765 comprises a layered construction comprising, from the distal end, a first PCB 766A on which a number of sensor components, e.g. magnetometers 766M, are arranged, a pair of battery connector discs 766B for a pair of coin cells, a second PCB 766C on which the majority of the electronic components are mounted (e.g. processor, transmitter/receiver and memory), and an upper disc 766D with a slot allowing the actuation rod portion 762 to contact and actuate a PCB mounted activation switch 766S, the five members being interconnected by flexible ribbon connectors.

The sensors comprise a number of magnetometers adapted to measure a magnetic field generated by the pen magnet 660M, this allowing rotational movement of the pen reset tube and thus the size of an expelled dose to be determined, see e.g. WO 2014/0161952. Further sensor means may be provided allowing the type of the device to be recognized, e.g. a light emitter and a colour sensor adapted to determine the colour of the pen release member, the colour serving as an identifier for the drug type contained in the prefilled pen device. The colour sensor and light emitter may operate with visible (to the human eye) light or light fully or partly outside the visible spectrum. The processor means may be in the form of a generic microprocessor or an ASIC, non-volatile program memory such as a ROM providing storage for embedded program code, writable memory such as flash memory and/or RAM for data, and a controller for the transmitter/receiver.

In a situation of use with the add-on device 700 mounted on the pen drug delivery device 600, the user starts setting a desired dose by rotating the dose setting member 711 (i.e. the add-on dose setting member) and with that also the dose release member 790. During dose setting the dose release member is biased towards its initial proximal position whereby it is rotationally locked to the inner assembly 780 via the locking splines 786, 796, this allowing the rotational movement of the add-on dose setting member to be transferred to the inner housing 761 and thus the pen dose setting member 680.

When a dose has been set the user will actuate the dose release member 790 by moving it distally against the force of the first bias spring 718. During the initial release movement the locking splines 786, 796 will disengage, this rotationally de-coupling the inner assembly 780 with the electronics from the dose release member 790 and thus from the add-on dose setting member 711. During the further release movement the dose release member 790 engages the actuation rod proximal end 763 (see FIG. 8A) whereby the sensor module 760 during the further release movement will be moved distally towards the pen release member 690 and subsequently into contact with the pen release member (see FIG. 8B). The engaging surfaces of the actuation rod 762 and the add-on dose release member 790 are optimized for minimal transfer of rotational movement. Finally, further distal movement of the add-on release member 790 will result in actuation of the pen release member 690 (see FIG. 8C in which the reset tube outer teeth 661 has been moved distally) and thereby expelling of the set dose (see FIG. 8D), the sensor module 760 thereby serving as an actuator.

In order to determine the size of an expelled dose the amount of rotation of the magnet 660M and thus the reset tube 660 is determined. More specifically, initial movement of the sensor module will activate a sensor switch which in turn will activate the sensor electronics 765 and start sampling of data from the magnetometers, this allowing a rotational start position of the magnet 660M to be determined prior to release of the expelling mechanism. During this period also the colour of the pen release member and thus the type of drug contained in the cartridge may be determined. As the reset tube 660 may rotate more than 360 degrees during expelling of a dose of drug, rotational movement during expelling will be detected and the number of full rotations (if any) determined. When it is detected that rotation of the reset tube has stopped, e.g. when a set dose has been fully expelled or when out-dosing is paused by the user, a rotational end position will be determined, this allowing the size of an expelled dose to be determined. Alternatively, the rotational end position may be determined when the sensor switch detects that the sensor module 760 has returned to its initial position.

→

As appears from the above description several events take place during axial movement of the sensor module and subsequently the combined axial movement of the sensor module and the reset tube. The sensor module is first moved away from its initial proximal position. After a relatively short travel the sensor switch will be activated and the sensor electronics turned on, this allowing the sensor system to start measuring values indicative of movement of the reset tube. Subsequently the sensor module is moved into contact with the pen release member from which point the sensor module and the reset tube move together axially. Further axial movement of the pen release member will release the spring-driven expelling mechanism and the reset tube will start rotating (which axial position may be termed an intermediate position). To ensure that the expelling mechanism is safely released the sensor module and reset tube will travel a further distance until the reset tube reaches a distal stop. Thus the reset tube will have started rotating as it travel towards the distal stop at which location the majority of rotational movement of the reset tube will take place. If the user allows the set dose to be fully expelled the reset tube will reach its rotational end position when in its distal-most position. When it has been detected that rotational movement has stopped a rotational end position of the reset tube can be determined. If the user desires to pause the expelling, the user will release pressure on the add-on release member and the reset tube will start moving proximally, however, until the reset tube reaches the intermediate axial position it will continue to rotate.

As initially disclosed, an aspect of the present invention provides that the sensor component (or as in the above-described embodiment the entire sensor module) moves axially together with the indicator (e.g. the reset tube provided with a magnet as in the above-described embodiment) during measuring of movement. Depending on the actual mechanical and electronic design of the system, the two structures may move axially together fully or partly during the measuring of movement. As appears from the above description of an exemplary embodiment, the sensor module moves together with the reset tube during rotation of the reset tube, this providing essentially constant measuring conditions for the sensor system during rotation. To provide corresponding essentially constant conditions for the sensor system when measuring the rotational start and end positions of the reset tube, these positions would have to be measured while the sensor module is in contact with the pen release member and thus moving together therewith. To ensure this the sensor module may be provided with switch or detection means allowing contact between the sensor module and the pen release member. Indeed, the initial rotational position of the reset tube would have to be determined before the expelling mechanism is released and the reset tube starts to rotate. Alternatively, the sensor module may be designed to measure the initial rotational position of the reset tube before the sensor module engages the pen release member. Although this would result in slightly different conditions for the sensor system when measuring the rotational start and end positions of the reset tube, such a set-up would provide more time for the rotational start position to be properly determined before the reset tube starts to rotate.

←

As appears, due to the rotational un-coupling of the inner assembly 760 from the outer assembly 780 during drug expelling, it is prevented to a high degree that movements of the outer parts of the add-on device will negatively influence the precise determination of rotational movement and rotational positions of the reset tube 660.

Turning to FIG. 9 a third exemplary embodiment of an add-on dose logging device 900 adapted to be mounted on a pen-formed drug delivery device 800 will be described in greater detail. The slightly modified drug delivery pen device 800 will be described with reference to FIGS. 10A and 10B.

Figure 7A:
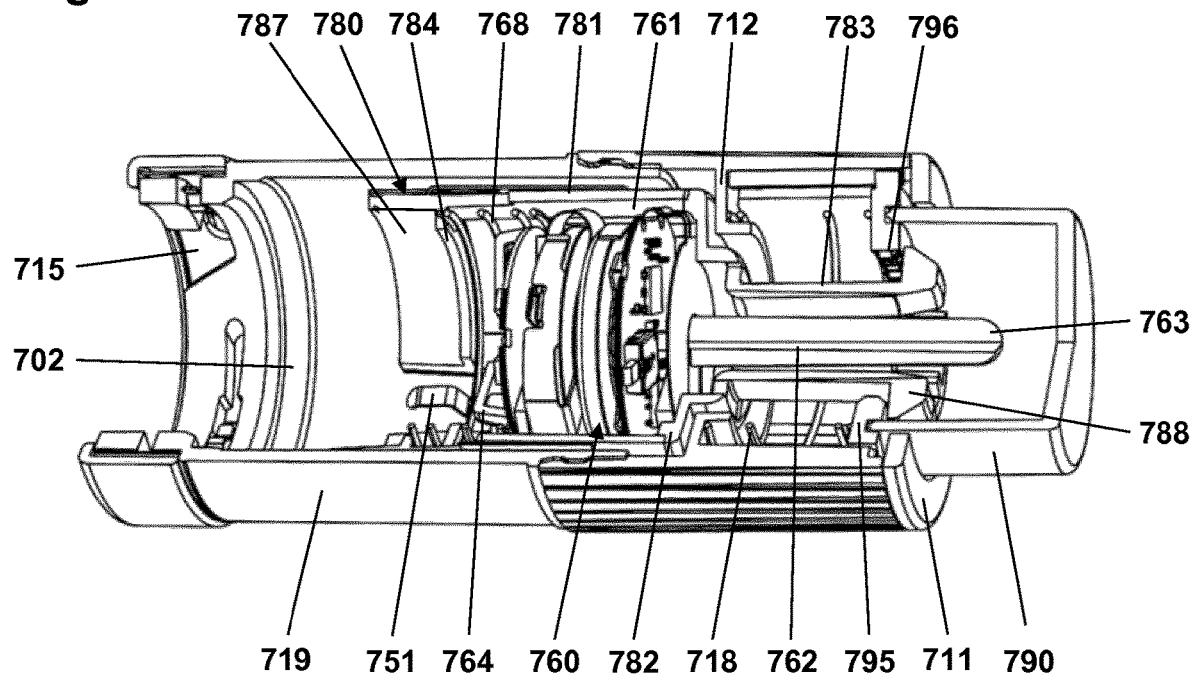
FIGS. 7A and 7B show cross-sectional views of the add-on device of FIG. 6.
Figure 7B:
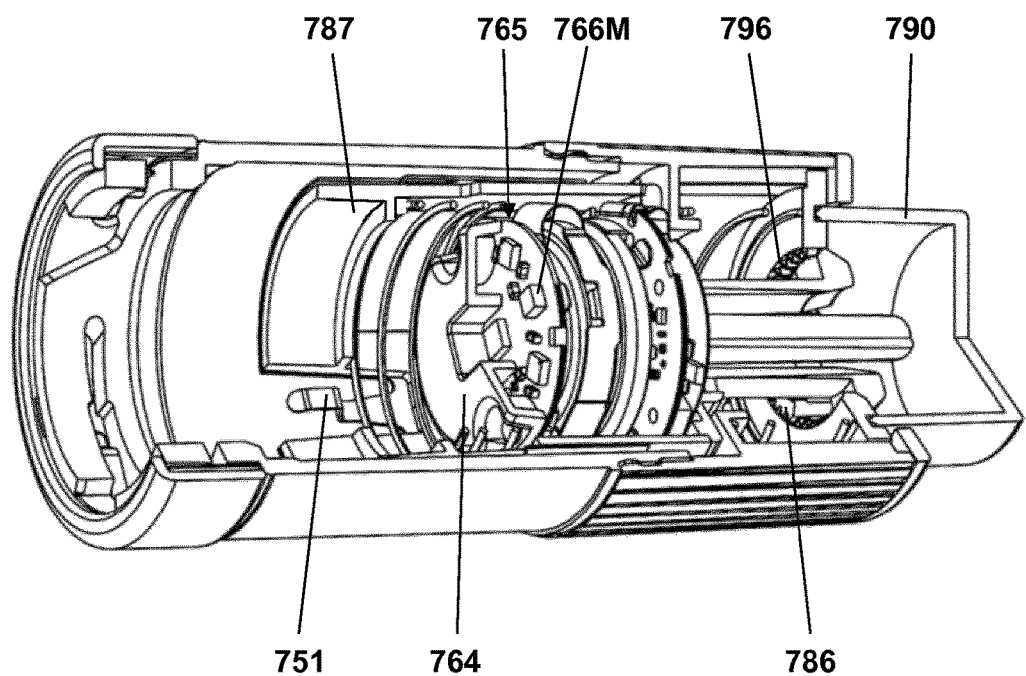
Figure 7C:
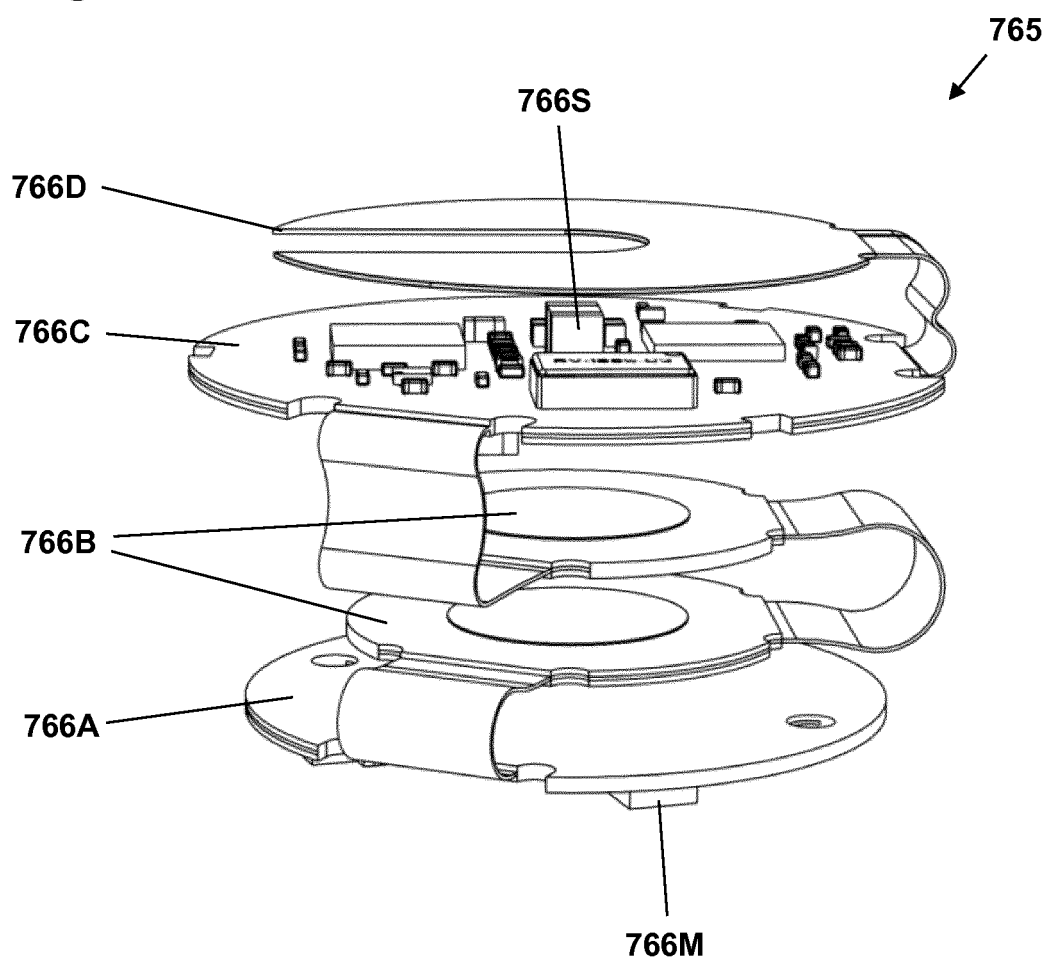
FIG. 7C shows in detail the electronic sensor circuitry incorporated in the add-on device of FIG. 7A, FIGS. 8A-8D show in sectional views and in different operational states an assembly comprising the add-on device of FIG. 6 mounted on a drug delivery device.

The add-on dose logging device 900 essentially corresponds to the add-on dose logging device 600 described with reference to FIGS. 6-8 and thus comprises an outer assembly releasably attachable to the drug delivery device housing, an inner assembly with a sensor module as well as a release member assembly. In contrast to the above described embodiments, the exploded view of FIG. 9 shows the individual components from which the assemblies are formed.

The outer assembly is formed by a distal housing coupling portion 901, a thereto attachable proximal housing portion 919, an add-on dose setting member 911 adapted to be mounted freely rotatable on the proximal housing portion, and a locking ring 916 adapted to be mounted in the dose setting member to enclose the release member assembly. A locking assembly comprises a release slider 908, a catch member 905, a bias spring 906 as well as a pair of return coil springs 909 for the slider, the locking assembly components being adapted to be mounted in the housing coupling portion 901.

More specifically, the distal housing coupling portion 901 comprises a cylindrical bore 902 adapted to receive a corresponding cylindrical coupling portion of the drug delivery pen device in a snug fit (see below). The bore is provided with a distally facing and axially oriented groove adapted to receive a pen housing locking protuberance 805 when the add-on device is axially mounted on the pen device. The proximal portion of the distal housing coupling portion tapers outwardly to a larger diameter and comprises a plurality of longitudinal ribs 907 each having a proximally facing end surface, the end surfaces serving as a distal stop for the inner assembly. The coupling portion 901 is adapted to cover the pen device display window when mounted and thus comprises a window opening 904 allowing the display window and thus the scale drum to be observed. Opposite the window opening a second opening 903 is provided adapted to receive the locking assembly components. The catch member 905 is pivotably mounted in the second opening and biased inwards by bias spring 906, this allowing the catch member to snap in place distally of the pen housing locking protuberance 805 when the add-on device is axially mounted on the pen device. As the locking means is arranged opposite the window opening 904 it is assured that the user can easily orient the add-on device rotationally during mounting. The release slider 908 is slidingly mounted in the second opening and biased in the distal direction by the return springs 909. When the user moves the release slider proximally this lifts the catch member 905 out of engagement with the housing locking protuberance 805 allowing the add-on device to be moved proximally and thus to be removed from the pen device. The proximal housing portion 919 is fixedly attached to the coupling portion 901 by e.g. welding, adhesive or snap means, and comprises a circumferential ridge 917 allowing the dose setting member 911 to be mounted freely rotatable by snap action. The dose setting member comprises a circumferential inner flange 912 which in an assembled state serves as a proximal stop for the inner assembly and a distal stop for the release member return spring 918, as well as a number of axially extending inner flanges forming a number of guide tracks 913 for the release member assembly. The locking ring 916 is adapted to be mounted axially fixed in the dose setting member by e.g. welding, adhesive or snap means as shown to thereby seal the gap between the dose setting member 911 and the cap member 998.

The inner assembly comprises a generally cylindrical inner housing member 981, a cylindrical locking member 950 adapted to be mounted on the inner housing member, and a proximal wall or lid member 982 adapted to be attached to the inner housing member to enclose the therein mounted sensor module. The wall member comprises a proximally extending tube portion 983 adapted to receive a proximal flange member 988.

More specifically, the inner housing member 981 comprises a larger diameter distal skirt portion 987 with a number of openings 989, a smaller diameter proximal portion with a number of axially extending wall sections 985 forming a number of guide tracks for the sensor module. The transition between the two portions forms an outer circumferential distal support 984 for a sensor spring 968 (see below). In the shown embodiment the cylindrical locking member 950 is formed from a single piece of sheet metal wherein is formed a first plurality of axially extending flexible dial locking arms 951 each having a proximal free end portion extending radially inwards, and a second plurality of axially extending flexible mounting arms 955 each having a proximal free end portion extending radially inwards. The mounting arms serve to snap into engagement with corresponding mounting openings 989 when the locking member is mounted on the inner housing member 981, this axially and rotationally locking the two members. The dial locking arms 951 distal ends are inwardly rounded and adapted to engage the pen dose setting member drive grooves 882 (see below). The proximal wall member 982 is adapted to be fixedly attached to the inner housing flanges by e.g. welding, adhesive or snap means and serves in an assembled state as a proximal stop for the sensor module. The proximally extending tube portion 983 comprises at the proximal end a pair of opposed radial extensions each comprising a plurality of axially oriented locking splines 986 adapted to engage corresponding splines on the release member in an assembled state. The proximal flange member 988 is adapted to be fixedly attached to the tube portion 983 by e.g. welding, adhesive or snap means as shown. The flange member comprises a central bore with a diameter smaller than the distal larger diameter end of the actuation rod 962 (see below), this providing a proximal stop for the actuation rod.

The sensor module 960 comprises a generally cylindrical sensor housing 961 in which electronic circuitry 965 with distally facing sensor components 966M (see FIG. 12B) is mounted, a spacer cap 964 adapted to be mounted on the sensor module housing distal end to cover and enclose the sensor components, as well as an actuation rod 962 adapted to be arranged in the wall member tube portion 983. A sensor module return spring 968 is adapted to be arranged between the inner housing member 981 and the sensor housing 961 to provide a proximally directed biasing force on the sensor module.

Figure 13A:
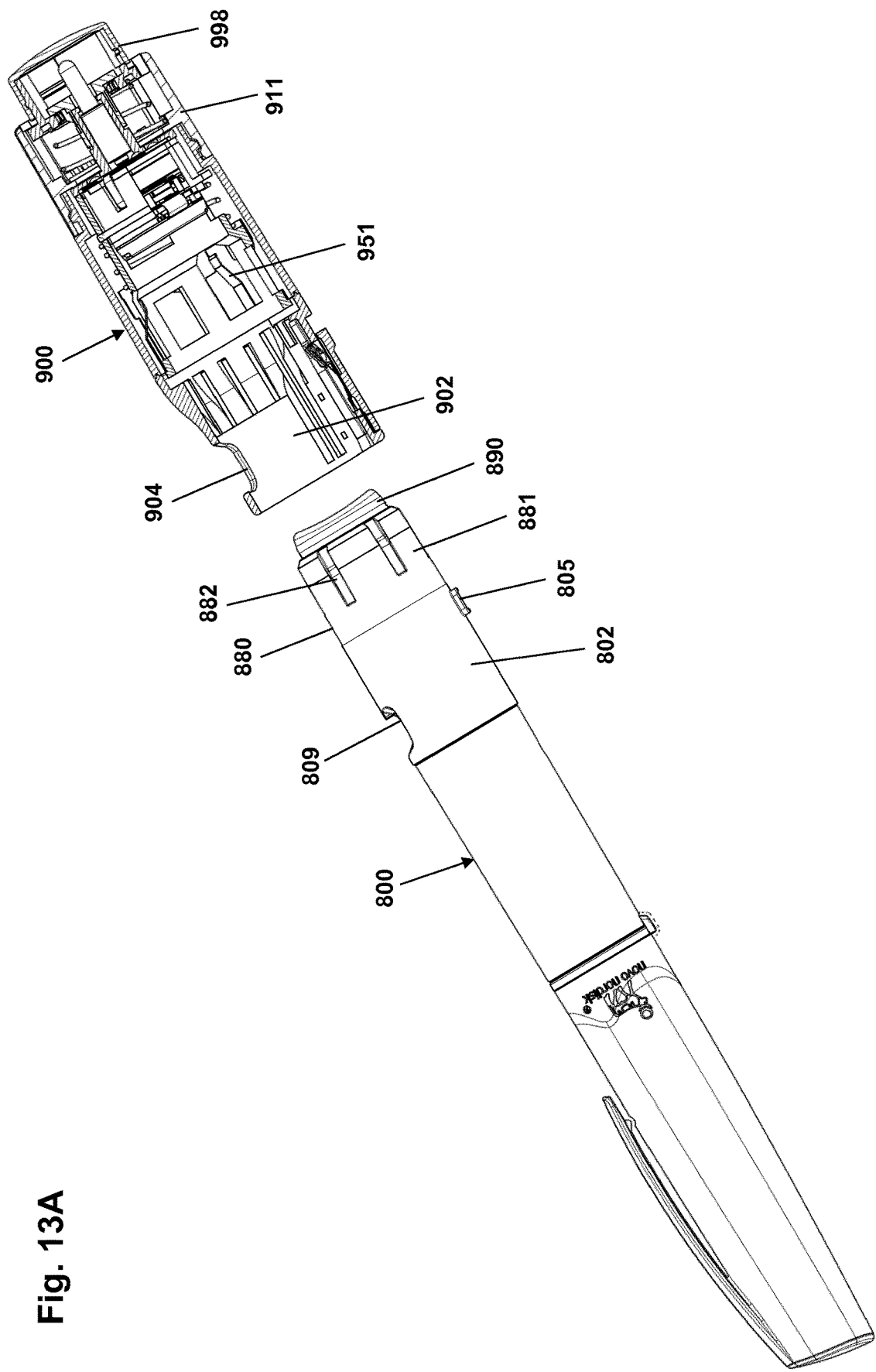
FIGS. 13A-13F show in cross-sectional views the third embodiment in a series of operational states.

More specifically, the spacer cap 964 is adapted to be fixedly attached to the sensor housing by e.g. welding, adhesive or snap means and serves in an assembled state to protect the sensor components and as a distally facing contact surface adapted to engage the pen device release member 890 (see FIG. 13A). The sensor housing comprises a number of radially protruding distal and proximal guide flanges 967 adapted to be received non-rotationally but axially free in the inner housing member guide tracks. The distal guide flanges also provide a proximal stop surface for the sensor spring 968. A distal stop for the sensor module is provided by the inner housing corresponding to the distal end of the guide tracks and/or the compressed sensor spring. The actuation rod 962 comprises a larger diameter distal portion allowing the rod to be freely received in the tube portion 983 and a smaller diameter proximal portion adapted to protrude through the bore in the flange member 988. The actuation rod comprises a rounded proximal end 963, the engaging surfaces of the actuation rod and the cap member 998 being optimized for minimal transfer of rotational movement. The sensor module comprises a proximally facing centrally arranged actuation switch 966, e.g. a dome switch, adapted to be actuated by the actuation rod.

The release member assembly comprises a body member 990 and a thereon mountable cap member 998. A release member return spring 918 is adapted to be arranged between the dose setting member flange 912 and the release body member 990 to provide a proximally directed biasing force on the release body member.

More specifically, the release body member 990 comprises a distal ring portion 994 with an inner circumferential array of axially oriented splines 996 adapted to engage the locking splines 986 on the tube portion 983 in an assembled state, as well as a number of radially protruding guide flanges 993 adapted to be received non-rotationally but axially free in the dose setting member guide tracks 913. The cap member 998 is adapted to be axially fixedly attached to the body member by e.g. welding, adhesive or snap means 995 as shown. In an assembled state flange member 988 serves as a proximal stop for the release body member 990 and the release member return spring 918 acts on the ring portion distal surface.

Figure 10A:
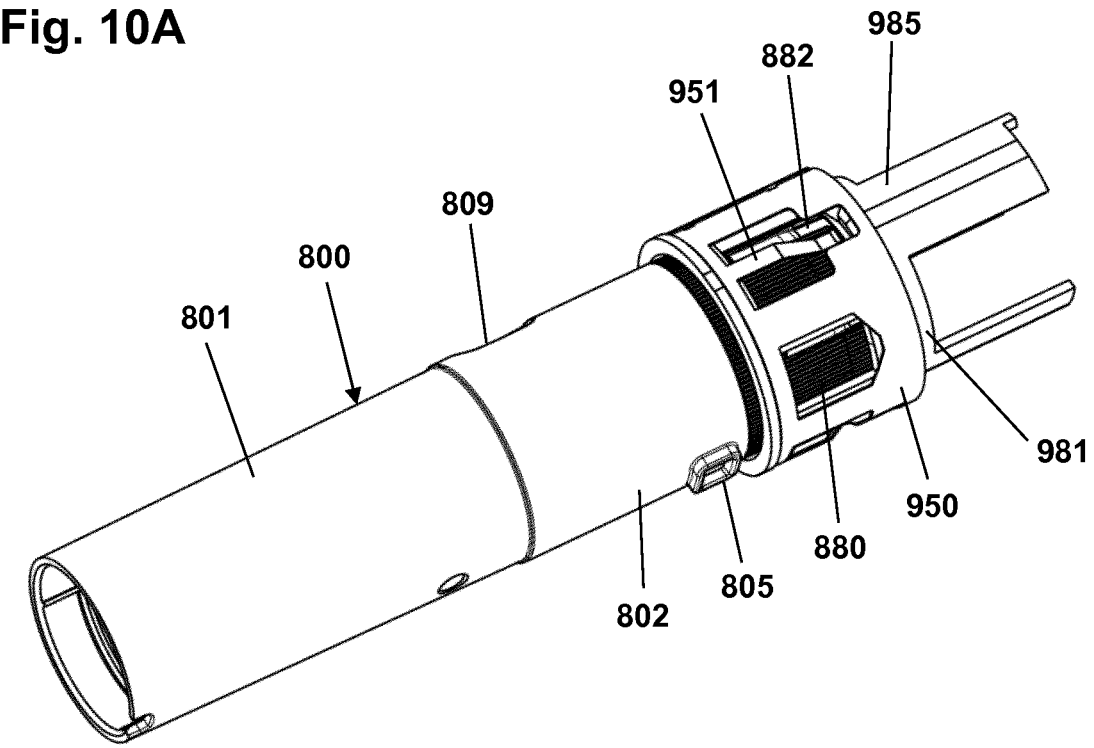
FIGS. 10A and 10B show in different states components of the add-on device of FIG. 9 mounted on a pen device.
Figure 10B:
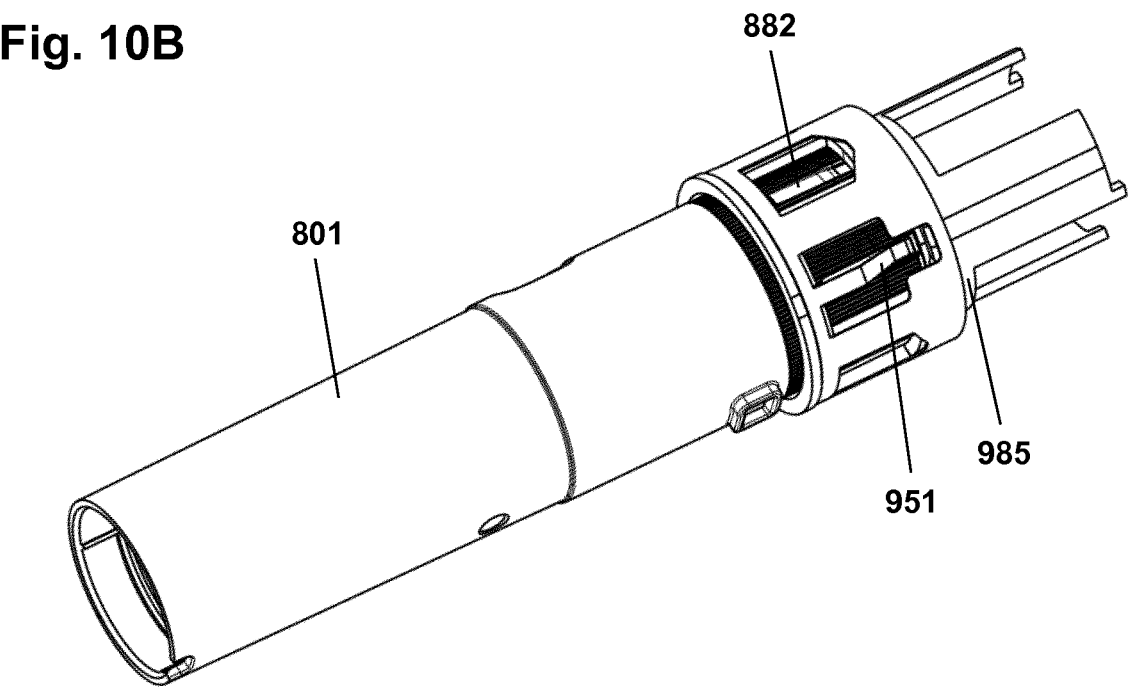

Turning to FIGS. 10A and 10B the proximal portion of a slightly modified pen drug delivery device 800 is shown in combination with the parts of the add-on device inner assembly providing rotational engagement between the add-on device and the pen dose setting member.

More specifically, the pen housing 801 generally corresponds to the embodiment of FIG. 6, however, instead of a slightly tapered housing the proximal coupling portion 802 of the housing including the window 809 has a "true" cylindrical form adapted to be received in the cylindrical bore of the add-on device. Alternatively, both structures may have a light taper. Further, the coupling means is in the form of a single locking protuberance 805 adapted to cooperate with the catch member 905 for easy axial mounting. Also shown is the dose setting member 880 having a generally cylindrical outer surface 881 (i.e. the dose setting member may be slightly tapered) which in the shown embodiment is textured by comprising a plurality of axially oriented fine grooves to improve finger grip during dose setting, as well as a number of axially oriented drive grooves 882 corresponding to the embodiment of FIG. 6.

As described above with reference to FIGS. 9A and 9B the inner assembly comprises a housing member 981 with a distal skirt portion 987 having a number of openings 989, as well as a cylindrical locking member 950 mounted thereon, the locking member comprising a number of flexible dial locking arms 951 and a number of flexible mounting arms (the latter not being shown in FIGS. 10A and 10B).

In FIG. 10A the inner housing 981 is shown in its axially mounted position (as determined by non-shown parts of the add-on device). Whereas the outer add-on housing 901 is mounted in a rotationally pre-determined position, this is not the case for the inner housing assembly which in an un-mounted state is allowed to freely rotate relative to the outer housing, this providing that the inner housing and thus the locking arms 951 are mounted in a "random" rotational position such that the locking arms are not rotationally in register with the dose setting member drive grooves 882. Additionally, although the dose setting member 880 has an initial "parked" rotational "zero" position corresponding to no dose having been set, it may have been set in a random position. Additionally, even when parked in the zero position slack in the dose setting mechanism may result in slight variations in the rotational position of the dose setting member drive grooves.

Thus, when the add-on device is mounted on the pen device the flexible dial locking arms 951 may be out of rotational register with the dose setting member drive grooves 882. However, due to the dial locking arms being flexible they will be moved outwards by the dose setting member and axially slide on the outer circumference of the dose setting member in parallel with the drive grooves, this as shown in FIG. 10A. As the resistance provided by the flexible locking arms is small the user will in most cases not notice what has happened during mounting of the add-on device and will not be aware of the fact that the add-on device has not yet rotationally engaged the pen device dose setting member. In the shown embodiment the free end of the locking arms 951 are oriented proximally, however, alternatively they may be oriented distally with the free end of the locking arms and the proximal edge of the pen device dose setting member 880 configured to move the locking arms outwards during mounting of the add-on device.

Subsequently, when the user desires to set a dose, the user will start rotate the add-on device dose setting member 911 and thereby the inner housing with the locking arms 951 which then will be rotated into register with the dose setting member drive grooves 882 and thus be allowed to flex inwardly to rotationally engage the drive grooves, this as shown in FIG. 10B. To assure that the locking arms will easily engage the drive grooves they are formed slightly narrower than the drive grooves. Further movement of the add-on device dose setting member 911 will then cause the pen device dose setting member to rotate correspondingly, this allowing the user to set and adjust a dose as normally. Indeed, in a number of cases the locking arms will be moved directly into the drive grooves.

The number and the mechanical properties of the locking arms 951 should be dimensioned to allow for safe and robust operation of the add-on device. To assure this the combined assembly, i.e. the pen device and the add-on device may comprise an over-torque mechanism in case the user tries to dial below zero or above the maximum settable dose amount. For the add-on device an over-torque mechanism may be incorporated in the spline engagement between inner housing assembly and the add-on dose setting member, however, in most cases such a mechanism for the add-on device can be dispensed with, as pen devices in general will be provided with an over-torque protection mechanism, e.g. as know from the FlexTouch® drug delivery pen. Indeed, the locking arms 951 and the dose setting member drive grooves 882 should be designed and dimensioned to withstand torque above the limit for the pen device over-torque mechanism.

Figure 11A:
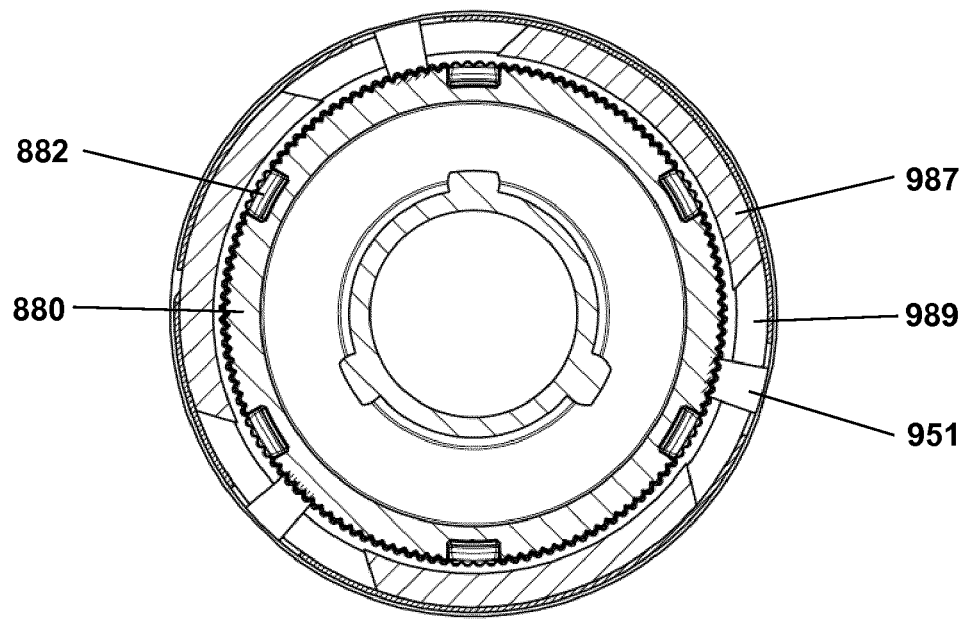
FIGS. 11A and 11B show cross-sectional views of the devices shown in FIGS. 10A and 10B, FIGS. 12A and 12B show in partial cut-away views the third embodiment in assembled state.
Figure 11B:
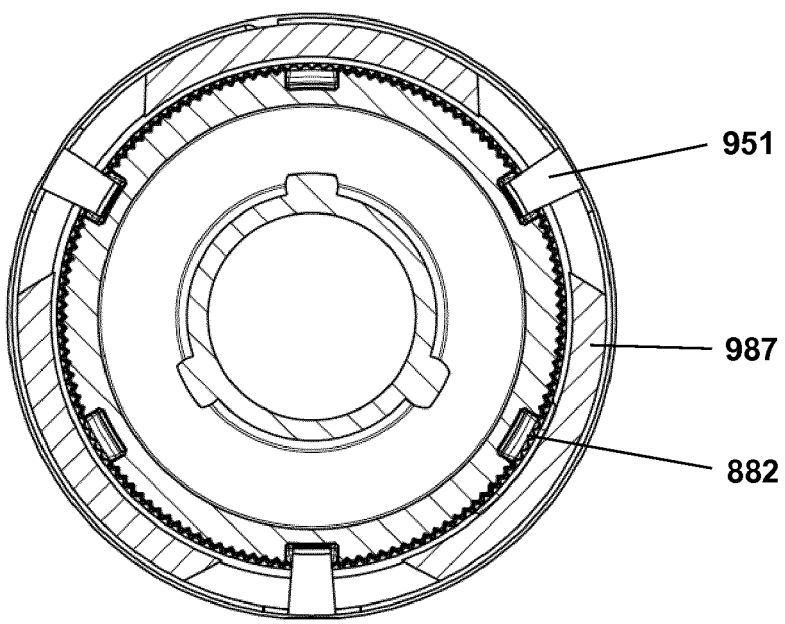

FIGS. 11A and 11B shows in cross-sectional views when the locking arms 951 have engaged the outer circumference of the pen device dose setting member 880 respectively have engaged the pen device dose setting member drive grooves 882.

Figure 12A:
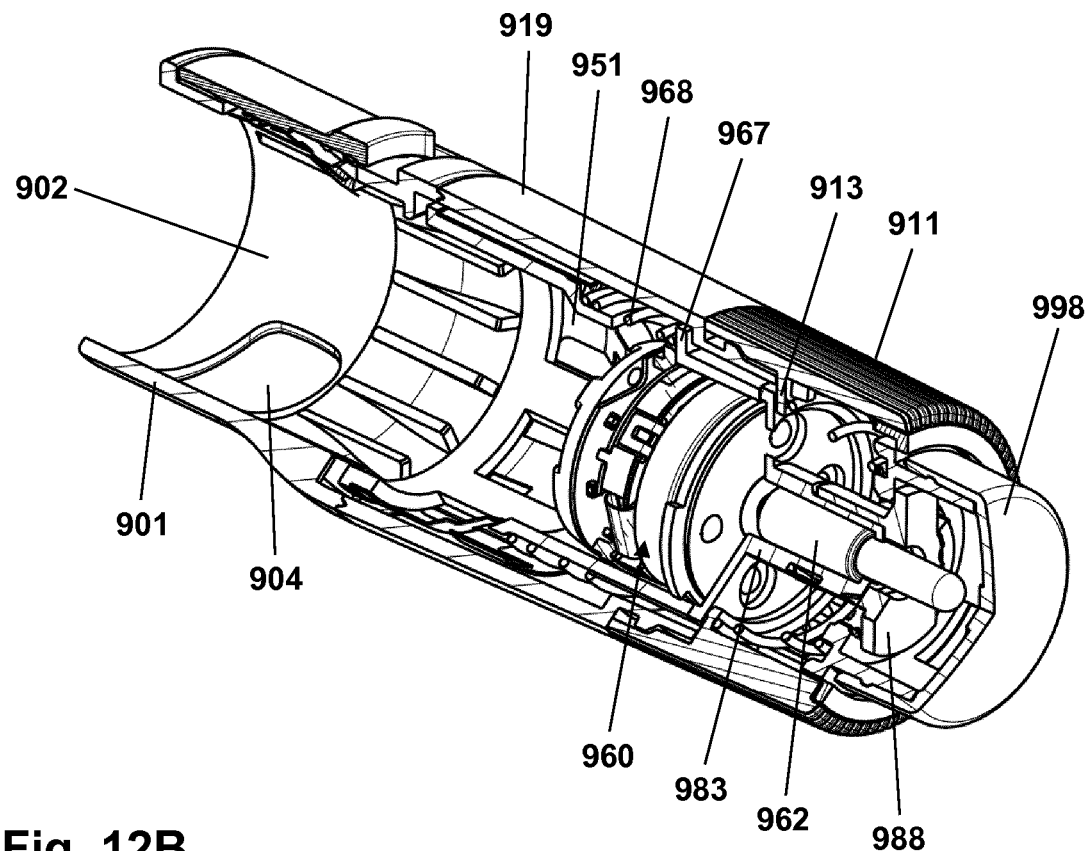
Figure 12B:
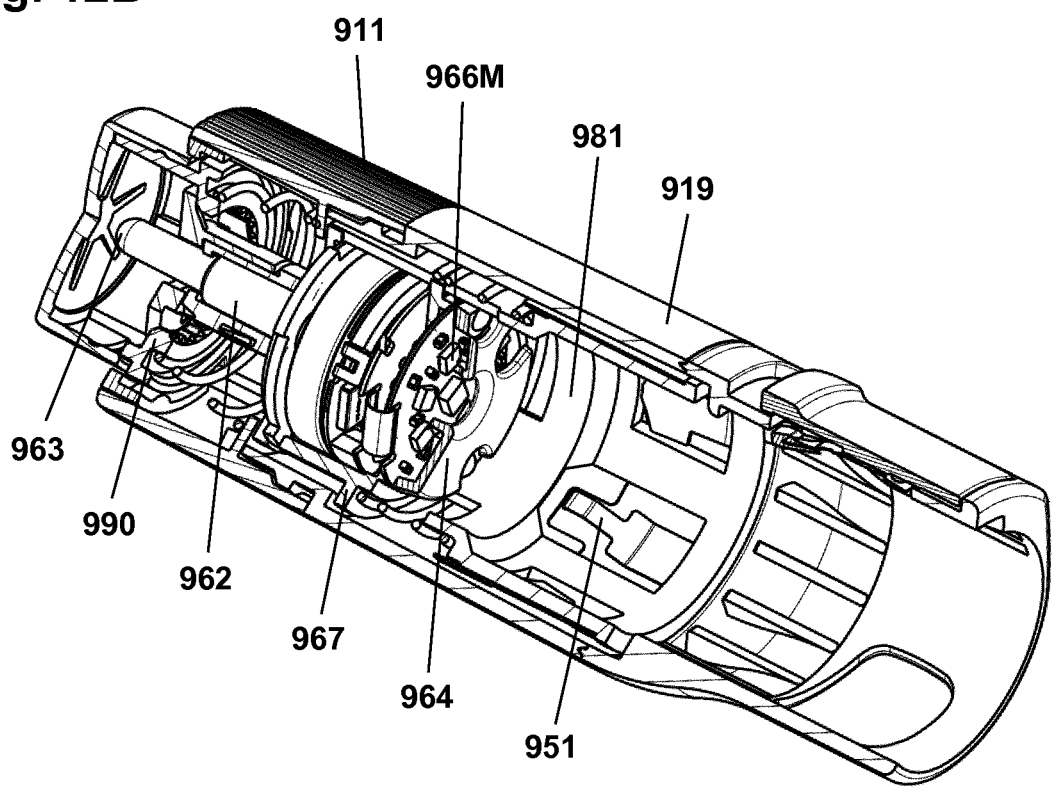

Turning to FIGS. 12A and 12B the components of FIG. 9A are shown in an assembled state corresponding to an initial non-mounted and non-actuated state.

More specifically, FIG. 12A shows the sensor module 960 arranged inside the inner assembly and being biased towards its proximal-most position by the sensor spring 968 acting between the inner housing spring support 984 and the sensor housing distal guide flanges 967. A dial locking arm 951 can be seen protruding into the interior of the inner housing skirt portion 987.

The release body member 990 is biased towards its proximal-most position by the release member return spring 918 acting between the dose setting member inner flange 912 and the ring portion 994 of the release body member. The actuation rod 962 is arranged inside the inner housing tube portion 983 and axially held in place by the flange member 988, an axial gap being formed between the actuation rod proximal end 963 and the distal surface of the cap member 998. The inner housing and the release member assembly are rotationally locked to each other via the splined engagement between the tube portion 983 and the release body member 990 (cannot be seen in FIG. 12A).

With reference to FIGS. 13A-13F different operational states of the third exemplary embodiment of an add-on dose logging device 900 in combination with a pen-formed drug delivery device 800 will be described. The shown pen device is in the form of a FlexTouch® prefilled drug delivery device from Novo Nordisk A/S.

FIG. 13A shows the add-on dose logging device 900 prior to being mounted on the pen-formed drug delivery device 800. As described above the drug delivery device comprises a proximal coupling portion 802 having a "true" cylindrical form adapted to be received in the cylindrical bore of the add-on device, a window 809, a locking protuberance 805 adapted to cooperate with the add-on device catch member 905, a dose setting member 880 having a generally cylindrical outer surface 881 with a number of axially oriented drive grooves 882, and a proximally arranged release member 890. The add-on device 900 comprises a cylindrical bore 902 adapted to receive the cylindrical coupling portion 802 of the pen device, a catch member 905 adapted to engage locking protuberance 805, and a window opening 904 arranged to be mounted in register with the pen device window 809, a dose setting member 911 and a dose release member 998. Projecting into the bore 902 a dial locking arm 951 can be seen. Corresponding to FIG. 12A the add-on device is in its initial non-mounted and non-actuated state.

Figure 13B:
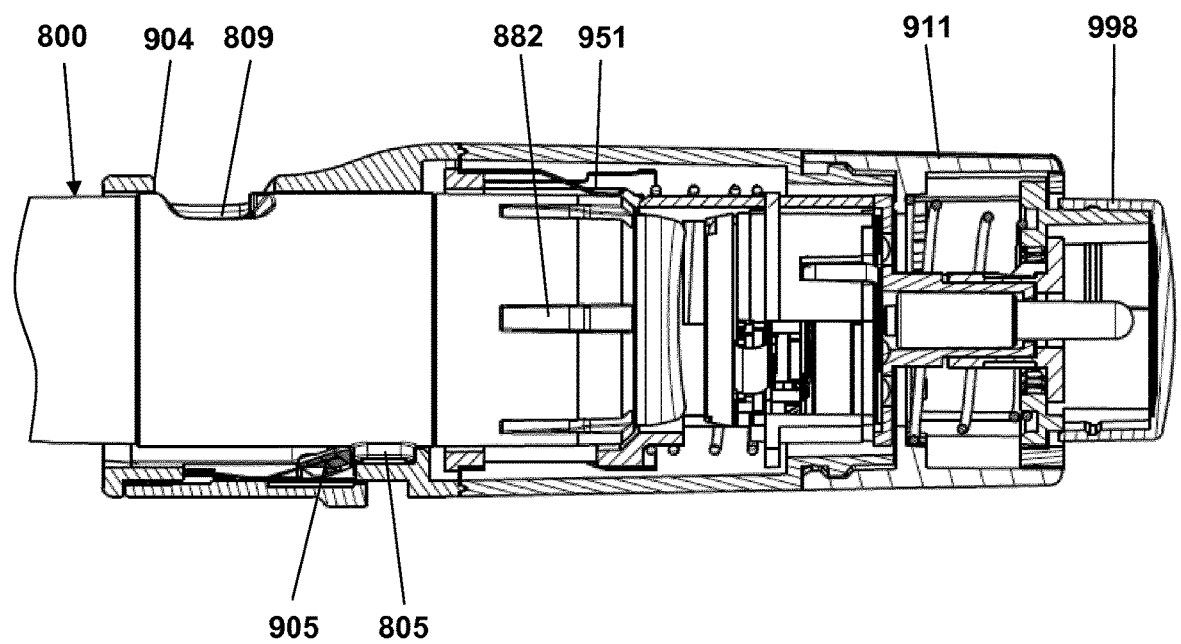

In FIG. 13B the add-on device 900 has been mounted on the pen device 800, with the catch member 905 seated distally of the locking protuberance 805 and the two windows 904, 809 in alignment. Corresponding to the situation shown in FIG. 10A the dial locking arms 951 have not yet engaged the drive grooves 882.

Figure 13C:
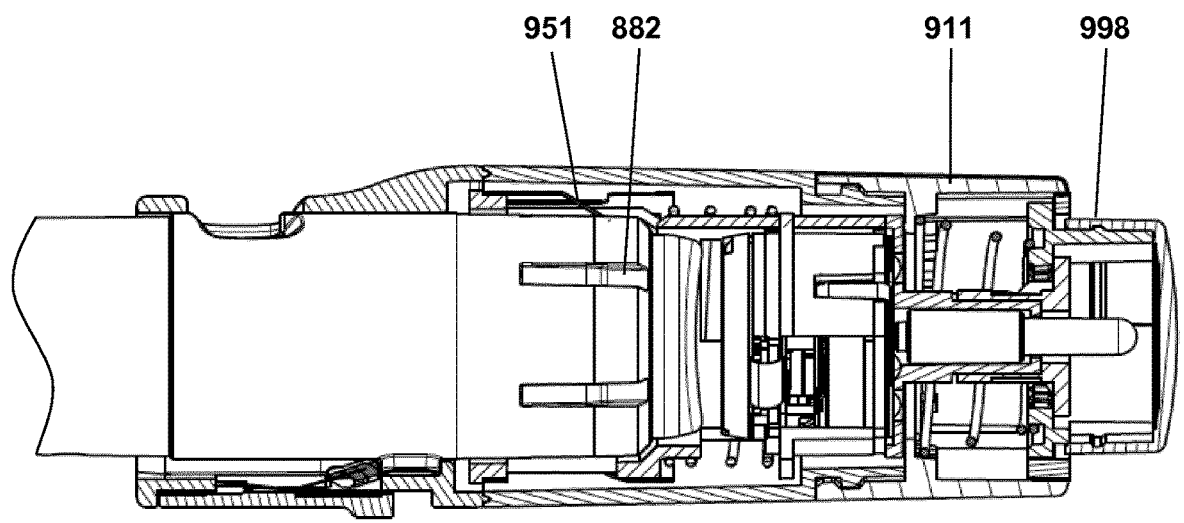

In FIG. 13C the add-on dose setting member 911 and thereby the inner assembly has been rotated, the dial locking arms 951 have engaged the drive grooves 882, and a dose has been set.

Figure 13D:
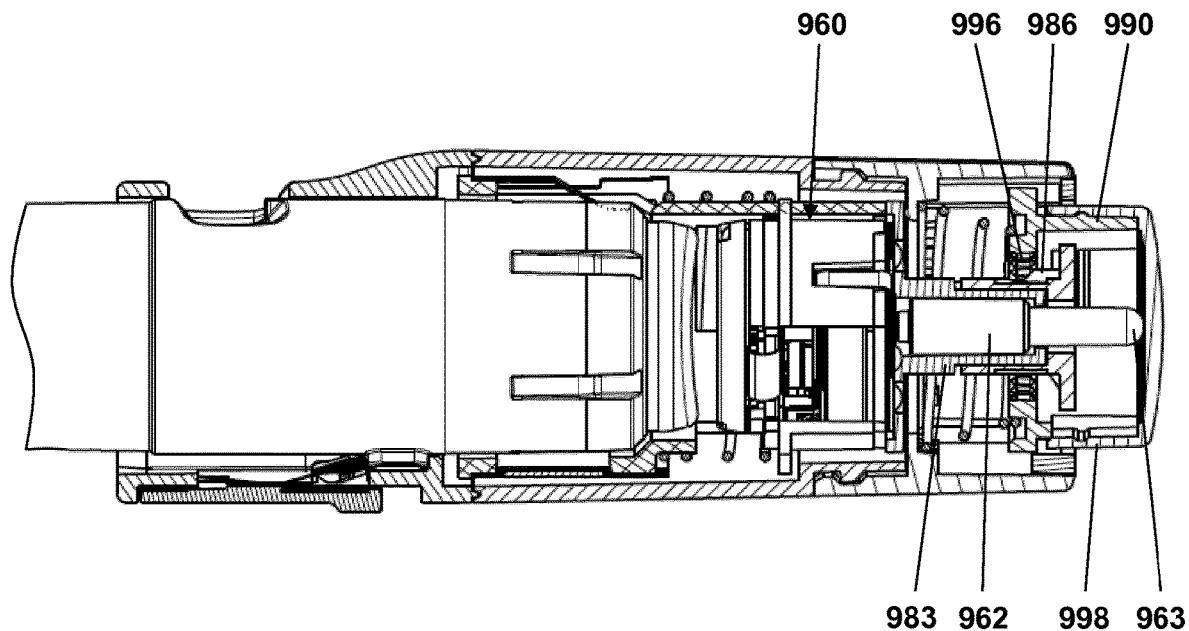

In FIG. 13D the add-on dose release member 998 has been partly actuated to just engage the actuation rod rounded proximal end 963, in which state the inner circumferential array of axially oriented splines 996 on the release body member 990 has disengaged the locking splines 986 on the tube portion 983, this rotationally decoupling the dose setting member 911 from the inner assembly and thus the sensor module 960. Further distal movement of the add-on dose release member will 998 start move the actuation rod 962 distally which initially will result in the proximally facing centrally arranged actuation switch 966 (see FIG. 9) being actuated by the actuation rod, this turning the sensor module into its operational state.

Figure 13E:
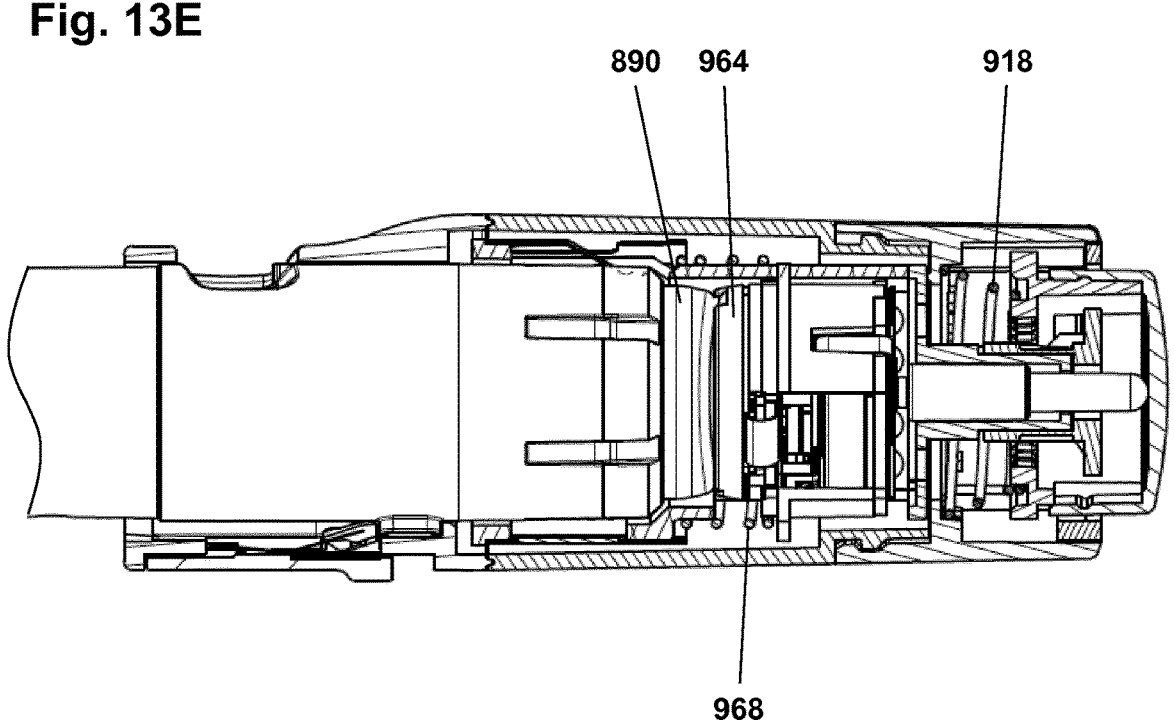

In FIG. 13E the add-on dose release member 998 has been further actuated to just move the sensor module spacer cap 964 into engagement with the pen device release member 890.

Figure 13F:
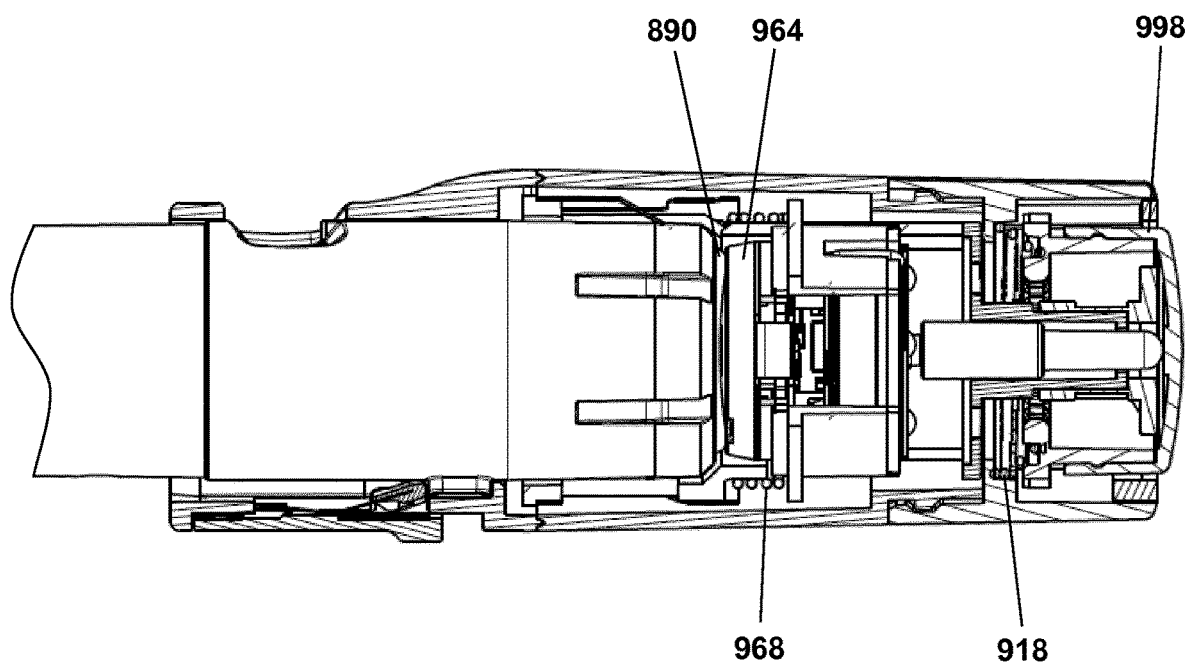

In FIG. 13F the add-on dose release member 998 has been fully actuated and the sensor module and thereby the pen device release member 890 have been moved to their distal-most operational positions, this releasing the expelling mechanism whereby the set dose of drug is expelled through a hollow needle mounted on the drug-filled cartridge. Determination of the expelled dose size may take place as described above with reference to FIGS. 8A-8D. When the set dose has been expelled the user may release pressure on the add-on dose release member 998 and the components will return to their initial axial positions due to the return springs 968, 918.

As appears, the axial movements performed by the sensor module and the reset tube relative to each other are the same for the embodiment described with reference to FIGS. 13A-13F as the embodiment described with reference to FIGS. 8A-8D, for which reason the same considerations apply in respect of the sensor module moving axially together, fully or partly, with the reset tube during measuring of movement.

Having described the mechanical concept and working principle of the add-on dose logging devices of FIGS. 5, 7A and 12A, the sensor and tracer system per se will be described in greater detail. Basically, the sensor and tracer system comprises a moving magnetic tracer component and a sensor system comprising one or more magnetometers, e.g. 3D compass sensors.

Figure 14:
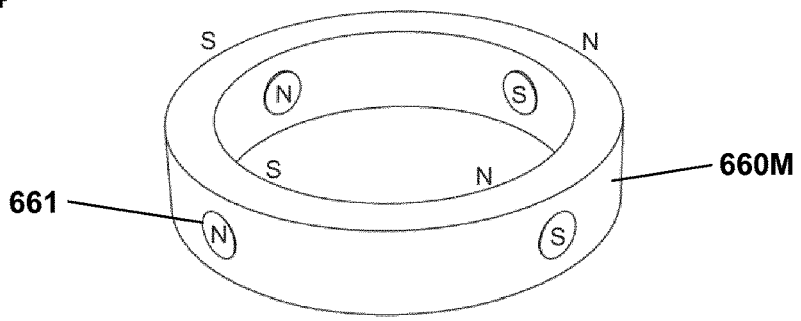
FIG. 14 shows individual dipole magnets arranged equidistantly in a ring-formed tracer component.

In an exemplary embodiment the magnetic tracer component is in the form of a multi-pole magnet having four poles, i.e. a quadrupole magnet. In FIG. 14 four dipole standard magnets 661 have been arranged equidistantly in a ring-formed tracer component 660M, the four separate dipole magnets providing a combined quadrupole magnet with the four poles offset by 90 degrees. Indeed, each of the dipole magnets are formed by a very large number of individual magnetic particles oriented in the same direction. The individual magnets may be arranged in the same plane or may be axially offset from each other.

Figure 15A:
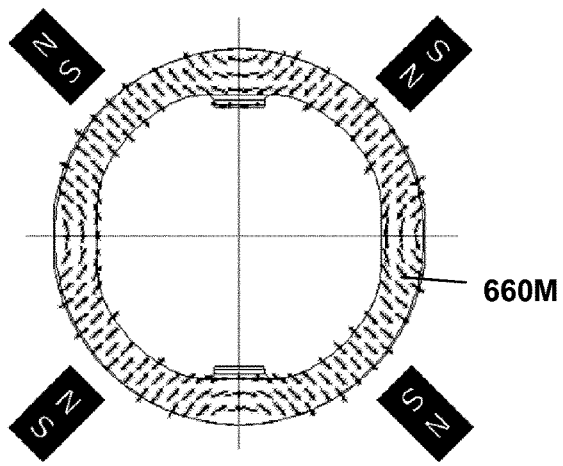
FIG. 15A shows a tracer component manufactured from a magnetisable material in combination arranged between individual magnets.
Figure 15B:
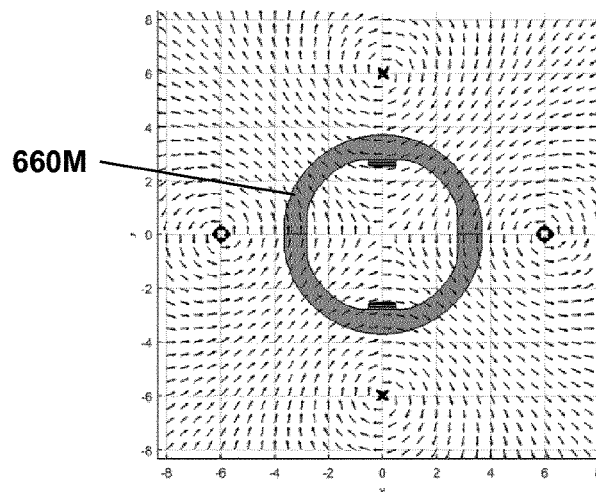
FIG. 15B shows a tracer component manufactured from a magnetisable material arranged in a multipolar electromagnetic field.

Alternatively, a multi-pole magnet 660M can be created by magnetization of a magnetisable material either by use of individual powerful magnets as shown in FIG. 15A, or through use of electromagnetic fields as shown in FIG. 15B.

Figure 16:
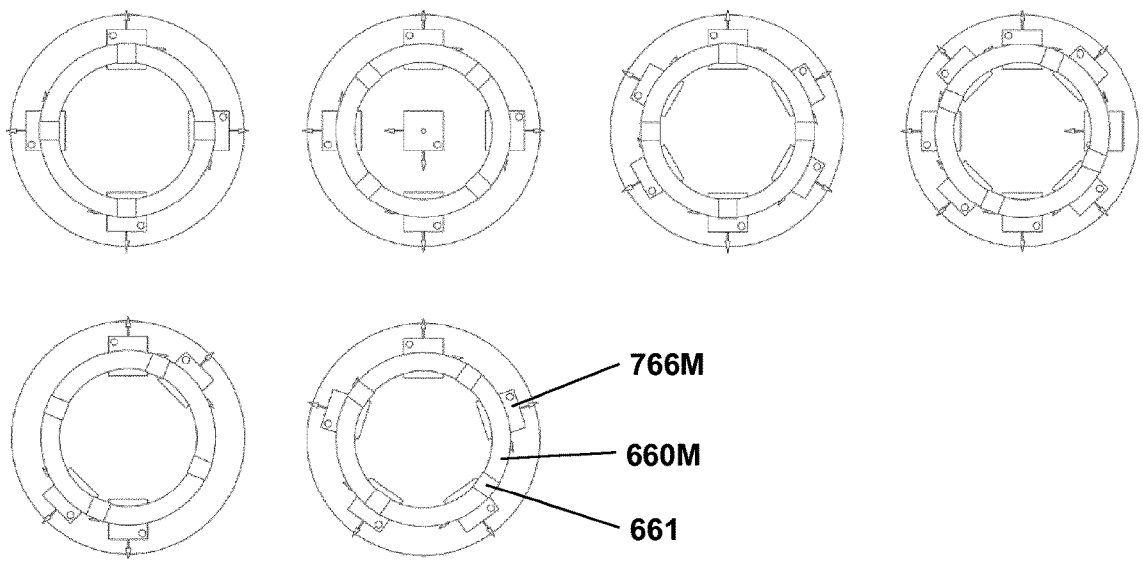
FIG. 16 shows different embodiments of a sensor system comprising magnetometers arranged relative to a tracer component.

A given sensor system may be using e.g. 4, 5, 6 or 8 magnetometers 766M arranged relative to a tracer component 660M as illustrated in FIG. 16. The sensors may be arranged in the same plane, e.g. as shown in FIG. 7B, or they may be axially offset from each other. The more sensors, the smaller spacing between the sensors and thus more data with a better signal-to-noise ratio can be gathered. However, the more sensors, the more data processing is required and the more power is consumed.

In some cases, not only disturbances from external fields need to be handled. The torque-providing spring for driving the dose expelling motor in the disposable device as described above may be magnetized when subjected to an external magnetic field and thus provide an internal disturbing magnetic field.

Where external disturbances may be cancelled out to a large extent by signal processing algorithms, because they influence all the sensors more or less equally and in the same direction, a magnetized torque spring will influence the sensors much like the tracer magnet and therefore be more likely to offset the measurements and cause errors.

Figure 17A:
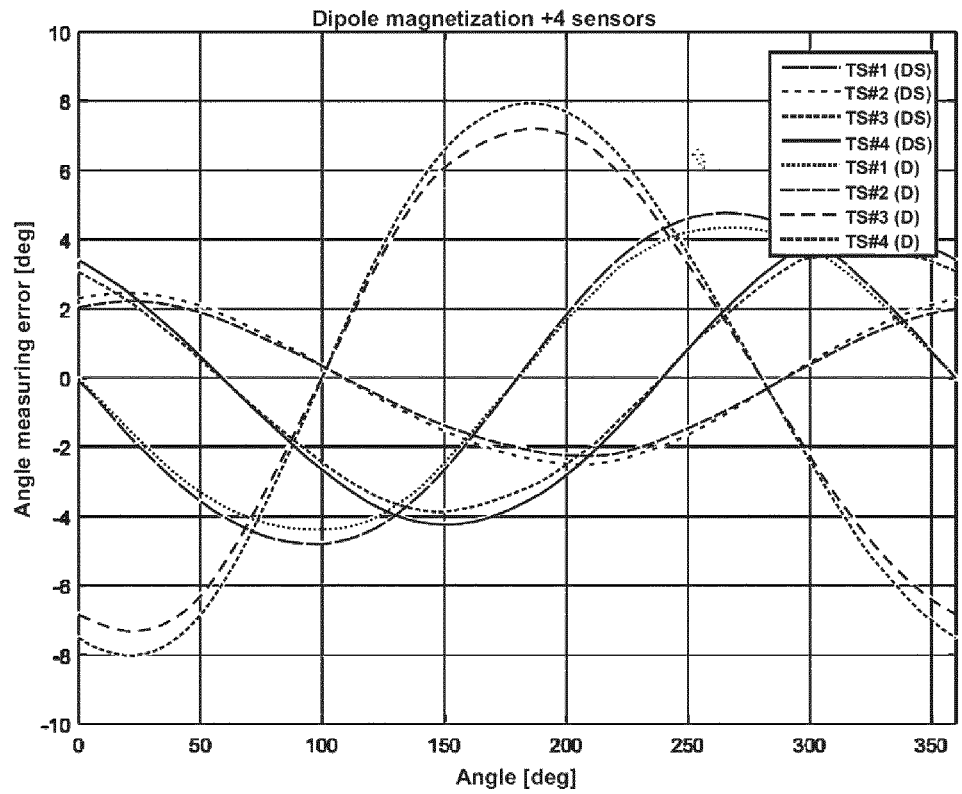
FIG. 17A shows angle measurements for a dipole tracer magnet in combination with a first sensor set-up.
Figure 17B:
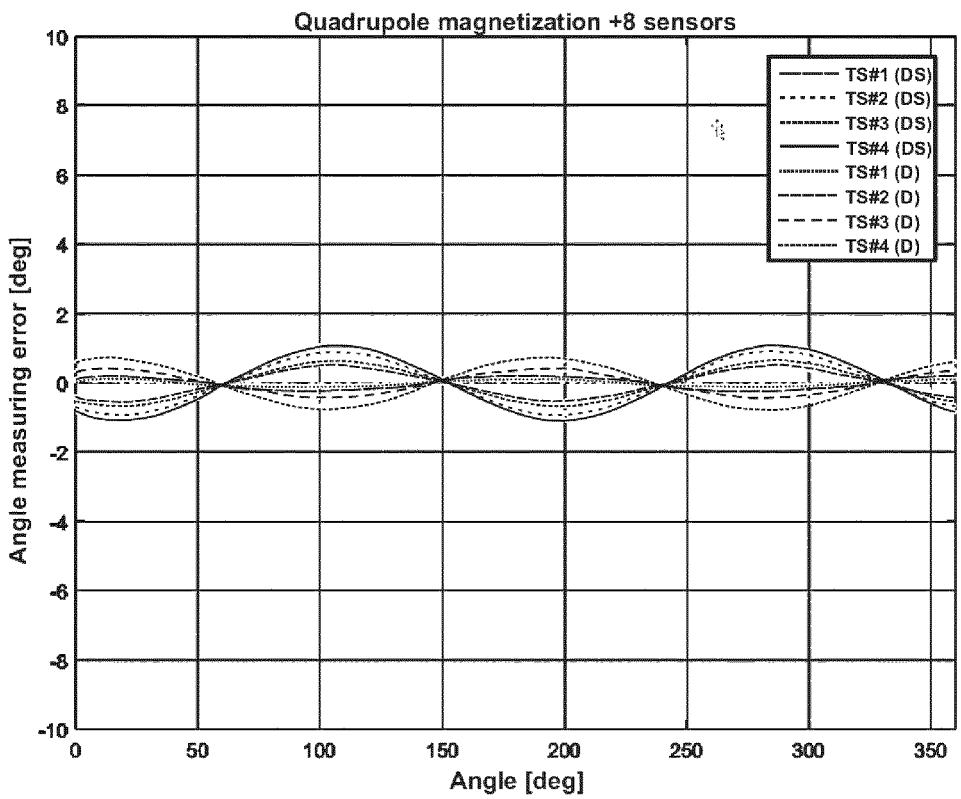
FIG. 17B shows angle measurements for a quadrupole tracer magnet in combination with a second sensor set-up.

However, as it can be seen from FIGS. 17A and 17B the use of a quadrupole tracer magnet instead of a dipole tracer magnet, significantly reduce the error in determining the position of the tracer magnet.

More specifically, FIGS. 17A and 17B show simulations of the influence of a magnetized torque spring at four different levels of magnetization (TS1-TS4) for both dose-setting (DS) and outdosing (D). FIG. 17A illustrates the calculated angle measuring error (i.e. the difference between the calculated angle and the true angle) for a dipole tracer magnet in combination with a 4 sensors set-up, and FIG. 17B illustrates the calculated angle measuring error for a quadrupole tracer magnet in combination with an 8 sensors set-up. Due to the sensors being closer to the tracer magnet during out-dosing (see e.g. FIGS. 8A and 8C) the angle error is slightly smaller during out-dosing. This said, in the above-described embodiment sensor measurements take place only during out-dosing. For the quadrupole tracer magnet 8 sensors were used as the smaller circumferential spacing between the individual poles in the quadrupole tracer magnet provides a higher input rate to the sensor system which can be more precisely captured by 8 instead of 4 sensors, however, comparable results would be expected for a quadrupole tracer magnet in combination with a 4 sensors set-up. As appears, use of a quadrupole tracer magnet reduces the angle error from ca. 4-8 degrees to ca. 0.5-1 degrees, roughly a factor of 8.

In the shown FlexTouch® drug delivery device the reset tube 660 and thus the tracer magnet 660M rotates 15 degrees for each unit of insulin expelled. Thus, a possible angle error in the 4-8 degrees range may result in an incorrect determination of the expelled dose amount.

The quadrupole tracer magnet is thus not only reducing the systems sensitivity to disturbances from external fields, but also from internal fields. This is an important aspect of using a multipole tracer magnet, since traditional magnetic shielding of external sources by use of an iron-containing metallic sheet may be used to reduce the influence of external fields, but may not be possible to fit between the tracer magnet and an internal disturbing magnetic field. Further, incorporating a magnetic shield would take up space and introduce additional costs.

Alternatively, this may be mitigated by using a spring of a non-magnetisable material, however, current spring-driven pens on the market today comprise a magnetisable torque spring and replacement may not be feasible due to other requirements of the spring.

Having described the structural set-up for a sensor assembly incorporating a rotating quadrupole tracer magnet, in the following an exemplary method of determining actual movements for such an assembly will be described.

Figure 18:
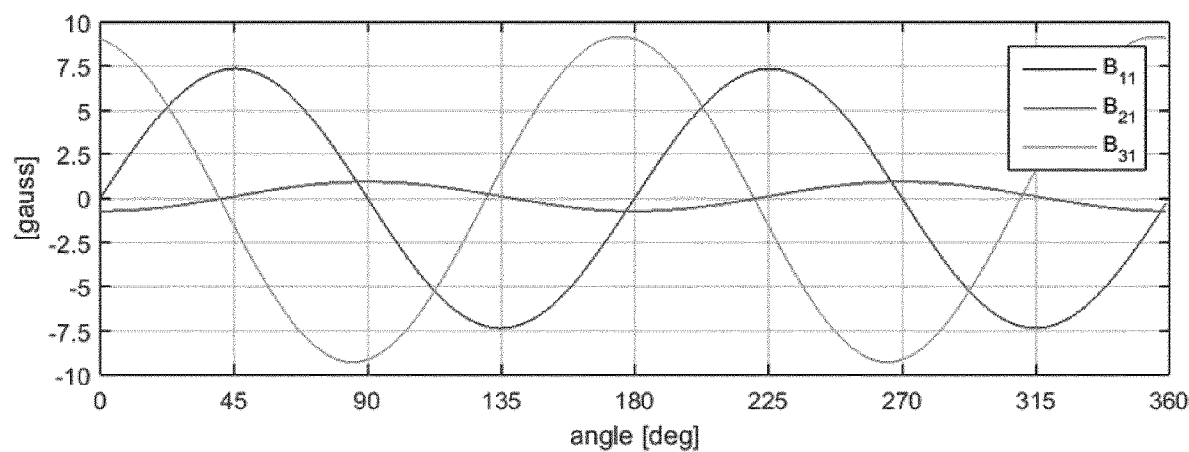
FIG. 18 shows signals from a quadrupole magnet over one full revolution of the magnet.

The signal from the quadrupole magnet is periodic with a period two over one full revolution of the magnet. This can be seen from FIG. 18 where the tangential, radial and axial field level is pictured.

Figure 19:
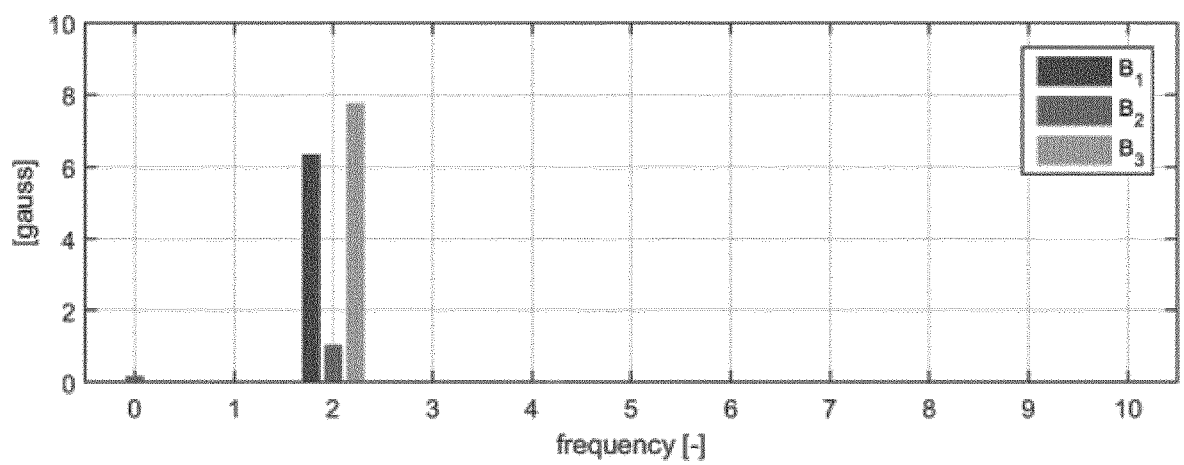
FIG. 19 shows a map of the frequency components of the signal from FIG. 18.

Mapping the frequency components of the signal, it is seen that all most the entire signal from the magnet fits into the frequency two signal, see FIG. 19.

Figure 20:
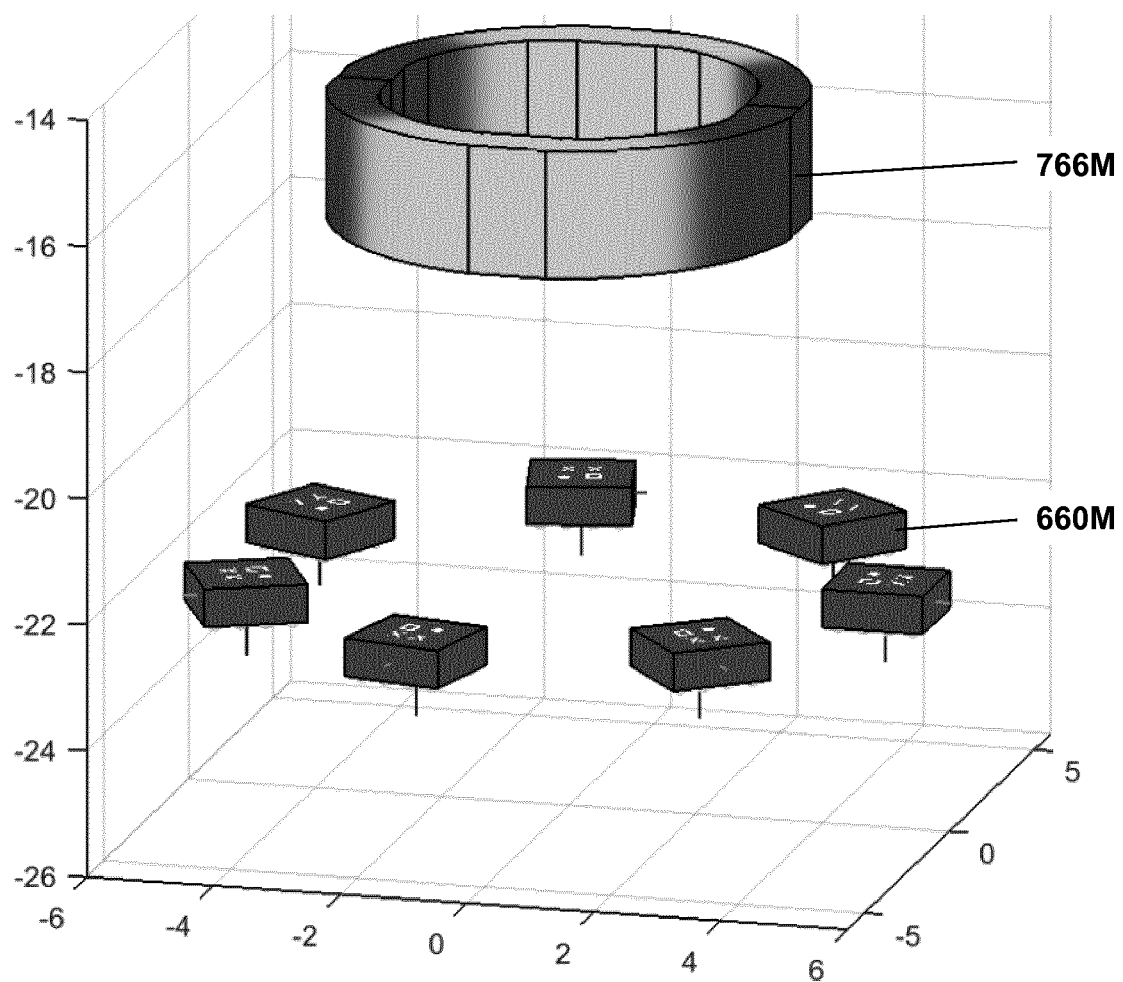
FIG. 20 shows an assembly of a quadrupole magnet and 7 magnetometers.

To determine a dose size utilizing at the quadrupole field, it is necessary to determine the static start and end angle of the quadrupole magnet. Since the magnet is static before and after the dose has been delivered, the field is sampled over space instead of sampled over time. In an exemplary embodiment a measurement system is configured with N=7 sensors with circular layout and equal spacing, see FIG. 20 showing sensor 766M placements relative to the quadrupole magnet 660M.

In order to determine the orientation or the magnet, a discrete Fourier transform (DFT) is computed on the field measured in the sensors $$\hat{B}_{jn} = \frac{2}{N}\sum_{k=1}^{N} B_{jk}\exp(-2\pi i k n/N).$$

Here $B_{jk}$ is the field in the j'th channel of the k'th sensor, j=1 is tangential field, j=2 is radial, and j=3 is axial, $i=\sqrt{-1}$ is the imaginary unit, and $\hat{B}_{jn}$ is the n'th frequency component of the signal in the j'th channel.

As described above, the signal from the quadrupole magnet is a period n=2 signal, and therefore we can determine the orientation of the magnet relative to the sensor board by looking at the phase of $\hat{B}_{j2}$, $$\varphi_j = a\tan 2[\operatorname{Im}(\hat{B}_{j2}), \operatorname{Re}(\hat{B}_{j2})]/2.$$

Because the samples of sines and cosines at different frequencies are orthogonal, any disturbance to the signal that is, e.g., period n=0, 1 or 3, will be filtered out by the Fourier transform.

This relates to both external as internal disturbances. An internal component in an auto-dose pen-injector is the metal torsion spring to drive the dosing mechanism. In the case of this being magnetized, the spring field will primarily look like a period 1 signal at the sensors position. External disturbances like a dipole magnet in the vicinity of the sensors will also tend to have a signal with period 0 or 1. Using the DFT, it is possible to filter out the disturbances from other frequencies and only determining the magnet orientation from the frequency 2 signal.

The combination of a quadrupole magnet and the DFT is therefore superior compared to a dipole magnet whose period 1 signal is similar to the frequency of common disturbances.

Using a DFT based algorithm gives a larger freedom to choose an arbitrary number of sensors, compared to a lookup based algorithm. The chosen number of sensors is preferably at least 5 due to the Nyquist sampling theorem. Besides that the number of sensors can be freely and actively used in order to filter out specific frequencies of the signal to prevent aliasing effects.

With reference to the above-described exemplary embodiments it has been described that initial movement of the sensor module will activate a sensor switch which in turn will activate the sensor electronics and start sampling of data from the magnetometers, this allowing a rotational start position of the magnet to be determined prior to release of the expelling mechanism. When it is detected that rotation of the reset tube has stopped, e.g. when a set dose has been fully expelled or when out-dosing is paused by the user, a rotational end position will be determined, this allowing the size of an expelled dose to be determined. Alternatively, the rotational end position may be determined when the sensor switch detects that the sensor module has returned to its initial position.

The sampling frequency should be chosen to reliably detect rotational movement and to be as power-efficient as possible. However, analysis of rotational speeds during out-dosing in a spring-driven device has shown that the rotational speed of the reset tube is not constant. Especially, it has been found that the rotational speed of the reset tube may be very high in the beginning of the expelling event. Two reasons for the high rotational speed have been identified. A first reason is that the cartridge rubber piston is in an uncompressed state before the out-dosing starts. When the energy in the drive spring is suddenly released, the rubber piston starts being compressed before it starts to move distally in the cartridge. When enough pressure is build up in the cartridge, the piston starts moving and the cartridge content starts to flow out of the needle. The compression of the plunger happens very fast, but is slowed down as it is being compressed.

A further reason is when there exists an air gap between the piston rod and the cartridge piston. This may occur e.g. if the user leaves a needle on the drug delivery device after use or it may be due to cycling temperatures. Since there is no reaction force from the rubber piston, the expelling mechanism rotates very fast until the piston rod hits the piston after which the above-described compression of the piston starts.

When detecting rotation of a component in order to estimate the expelled dose volume, it is important to accurately count all rotations. If not, this can lead to a smaller dose being estimated, which could cause the user to take another dose and have a severe overdose.

Figure 23A:
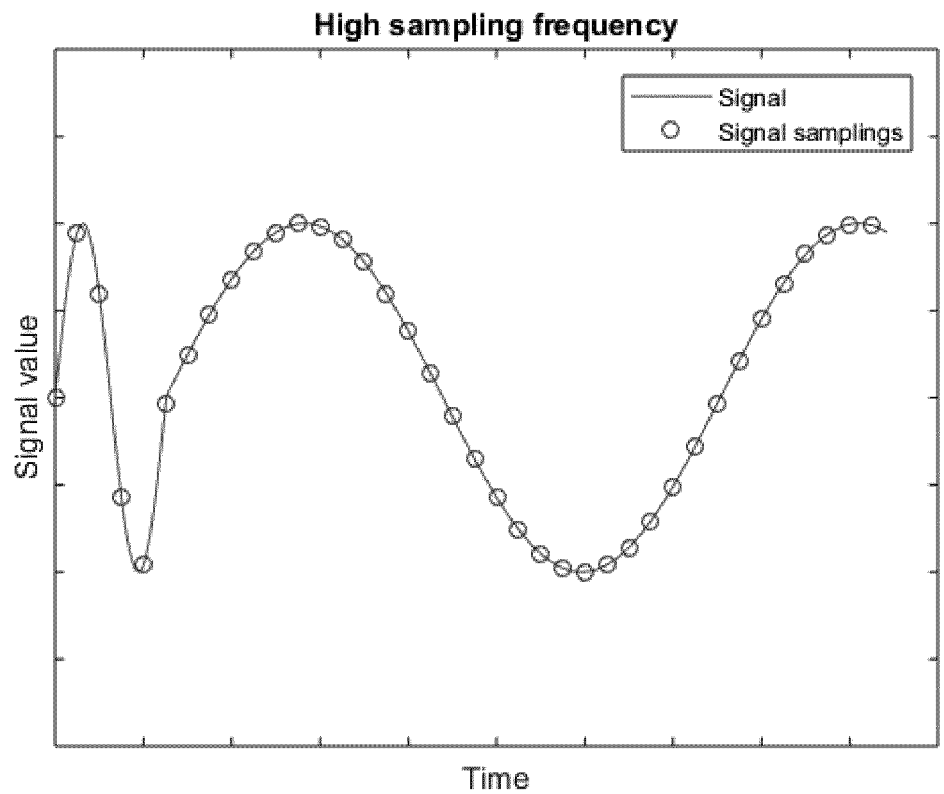
FIGS. 23A and 23B show first and second examples for a static sampling strategy.
Figure 23B:
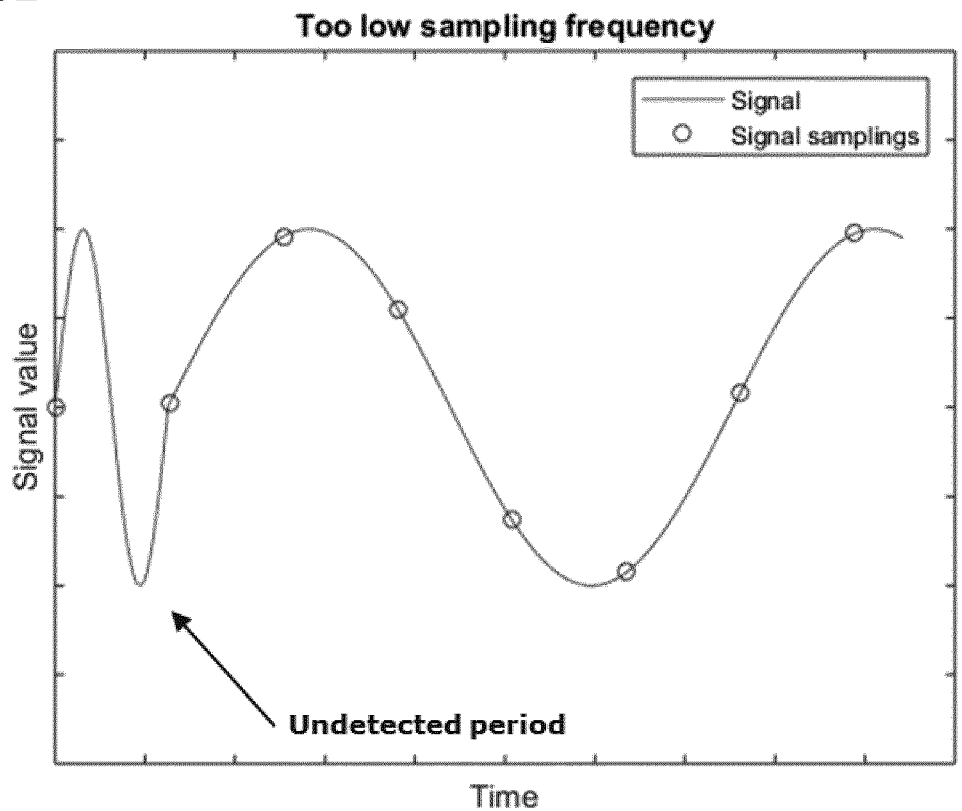

If one uses an active sensor to sample the position of the component, e.g. by measuring the change in magnetic field, the high rotational speed requires a high sampling frequency in order to see all rotations. However, using a high sampling frequency can be very power consuming and can collect large amounts of data that needs to be stored. This can lead to high power use and running out of memory issues. This is especially an issue for memory devices provided with a non-replaceable energy source. In contrast, if the frequency is too low, one or more cycles of the signal might go undetected. The two situations are illustrated in FIGS. 23A and 23B respectively.

Addressing this issue, a dynamic sampling scheme may be used based on (i) knowledge of system behaviour, and (ii) sensing of actual rotational speed of the measured component. The system can be expected to behave as follows: Staring with a period of fast rotation of the expelling mechanism, followed by a period with normal/moderate rotation speed, and ending in a state with no rotation when a set dose has been fully expelled—or the expelling has been stopped by the user. Thus an adaptive sampling scheme can be implemented that adapts the mode as the rotational speed changes and starting at a high sampling frequency.

Figure 24:
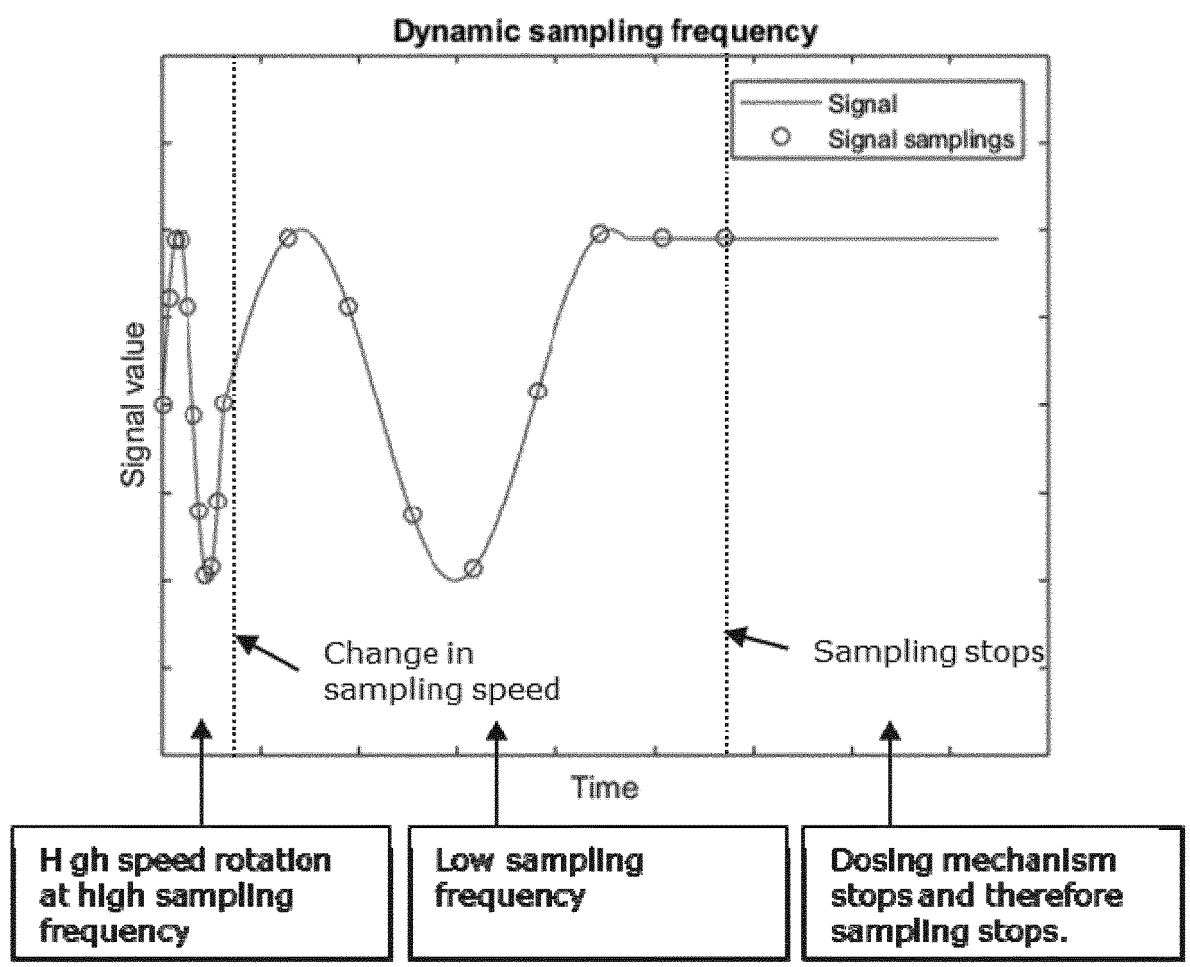
FIG. 24 shows an example of a dynamic sampling strategy.

Corresponding to the above-described embodiments an exemplary use scenario is illustrated in FIG. 24. More specifically, after having set a dose amount of drug to be expelled the user presses the add-on release button and the subsequent axial travel of the sensor module triggers the sensor switch and starts continuous sampling and evaluation of rotational speed with the sampling frequency initially being set to "high". The sensor module subsequently engages the pen release button and releases the pen expelling mechanism. Due to plunger compression and/or an air gap between piston and the piston rod, the expelling mechanism may initially rotate at a high speed for a shorter or longer period. When the expelling mechanism subsequently slows down it can be detected that the rotational speed is lower than a first threshold (Threshold$_1$), this allowing the sample frequency to be adjusted to "low". Ultimately, when it is detected that rotation has stopped, i.e. rotational speed is lower than a second threshold (Threshold$_2$), the sampling stops in order to save power. In other embodiments more than two thresholds may be used.

Indeed, other adaptive sampling schemes may be utilized. For example, the sampling frequency may vary continuously with the rotational speed for a predefined range of rotational speeds.

In the above disclosure the issue of both external disturbing magnet fields as well as an internal disturbing magnet field from the pen device torque spring have been addressed by the use of a quadrupole tracer magnet in combination with a sensor array comprising a number of magnetometers. In the following this issue is addressed by a different approach which may be used as an alternative or in addition to the above-described quadrupole design.

Using magnetic shields to shield magnetic systems from outside interference is commonly known and used. Normally shields are used as a barrier to either contain magnetic fields and prevent them from influencing other systems, or as a barrier to contain a system and shield it from being influenced by outside (unshielded) magnetic fields. Internal components of the system, that may introduce disturbing fields, are normally placed outside the shielded volume of the system. Indeed, it may be possible to incorporate a shield in a drug delivery device comprising a drive spring manufactured from a magnetisable material, however, as this may require a major redesign of the pen device this may not be a cost-effective option.

The technical problem to be solved, is thus to provide a magnetic shield preventing/reducing internal magnetic fields from disturbing the measurements of the magnetic sensors in a capturing device or assembly based on magnetometers. Additionally, such a shield may also serve to prevent/reduce the disturbances from "normal" external magnetic fields.

The suggested solution is to introduce a shield of mu-metal, to not only shield the sensor system from external magnetic fields, but also divert any unintended internal magnetic field introduced by the torque spring towards the shield and reduce the disturbance of the field of the tracer magnets. By reducing the strength of the disturbing field from the torque spring it may enable the use of fewer sensors and thus lower signal processing requirements to obtain required accuracy and redundancy, and thereby reduce both costs and power consumption.

Mu-metal is a nickel-iron soft magnetic alloy with very high permeability. It has several compositions, with approximately 80% nickel, 15% a few percent molybdenum and in some compositions a little copper and chromium. Mu-metal is very ductile and workable and can easily be formed into thin sheets needed for magnetic shields. However, mu-metal objects require heat treatment after they are worked into their final form.

Magnetic shields made with mu-metal works by providing a path for the magnetic lines around the shielded area instead of blocking them. The mu-metal sort of offers an "easier" path than thought the air with much lower relative permeability and thus diverts the magnetic field. However, mu-metal has a much lower saturation level and are thus not suitable for shielding against stronger magnetic fields.

Figure 8A:
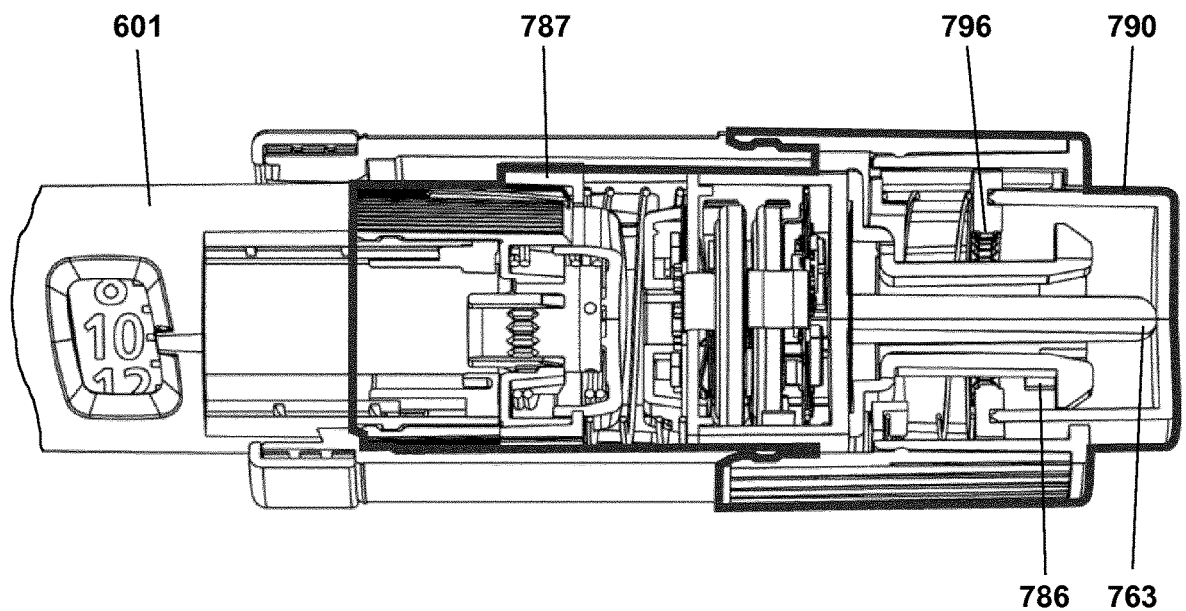
Figure 8B:
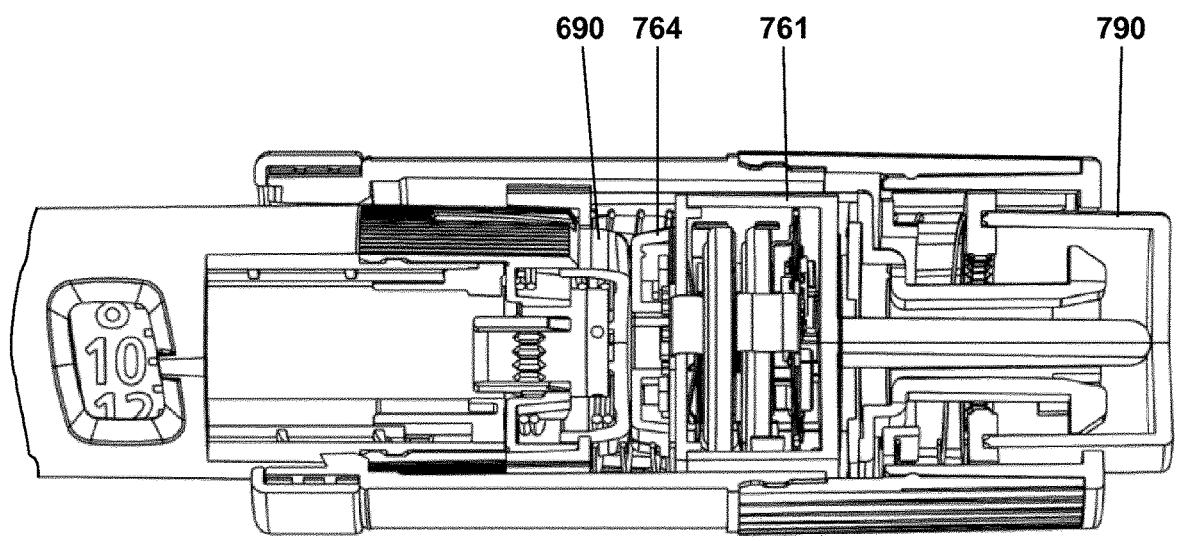
Figure 8C:
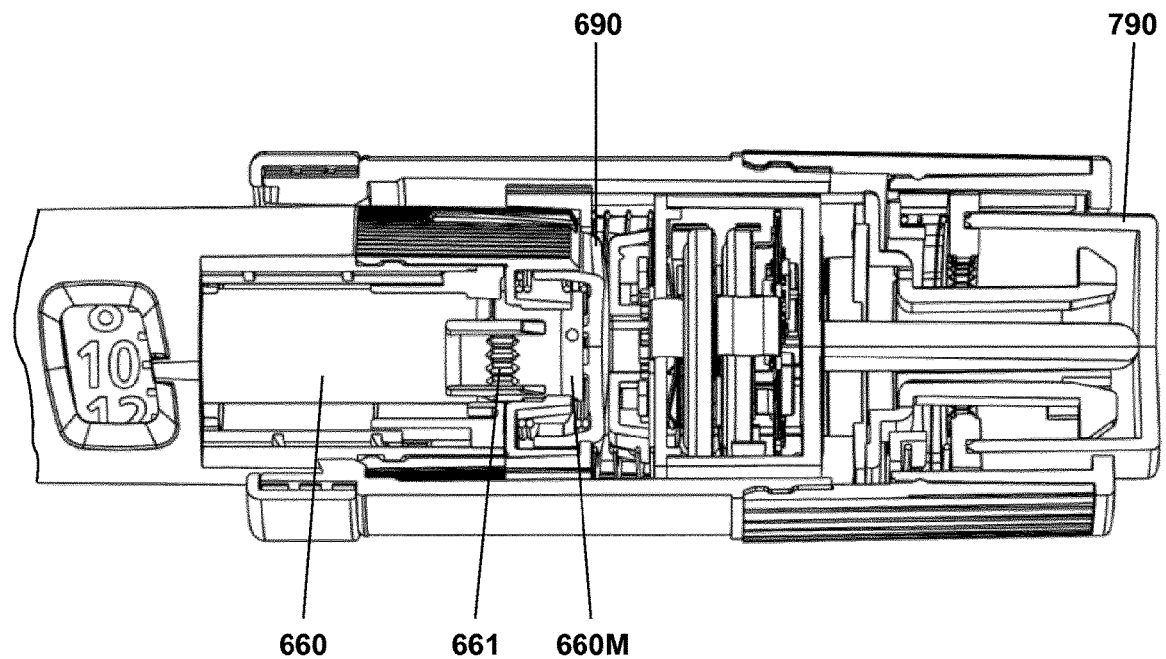
Figure 8D:
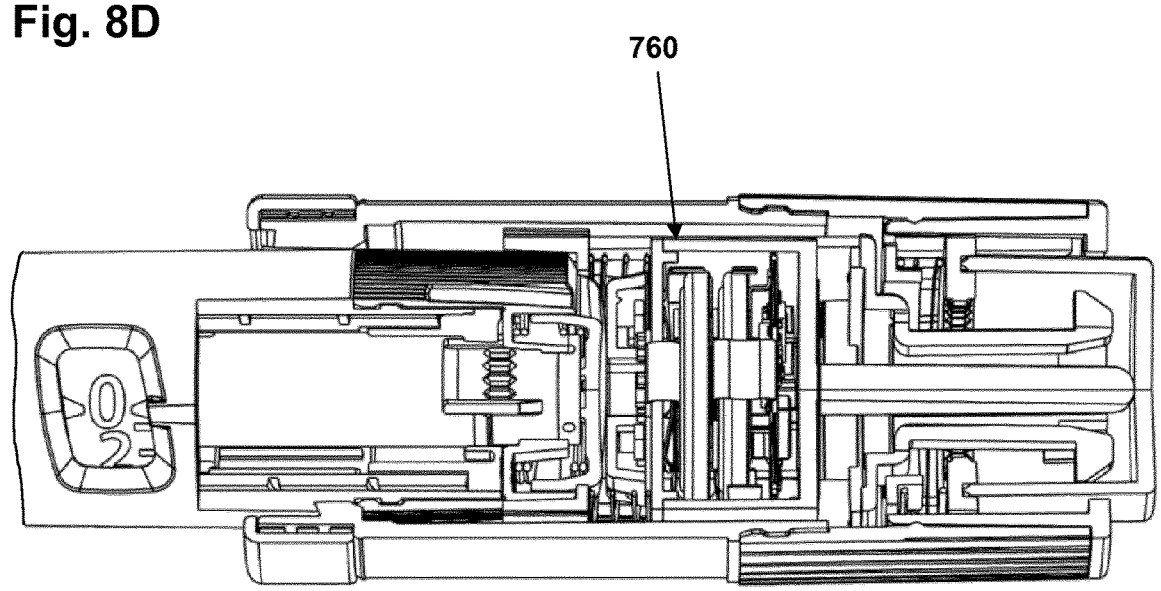
Figure 21:
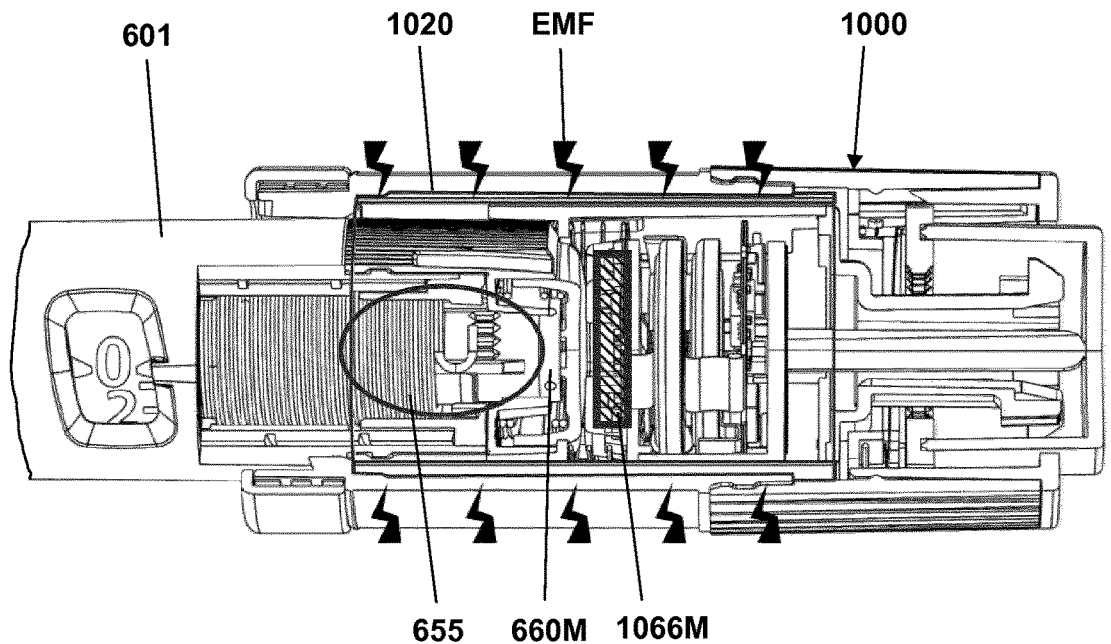
FIG. 21 shows a further embodiment of add-on device mounted on a drug delivery device.

FIG. 21 shows an assembly essentially corresponding to the assembly shown in FIG. 8A albeit with the drug delivery device torque drive spring 655 shown, the add-on dose logging device 1000 being provided with a cylindrical shield 1020 made of mu-metal covering the axial length of the sensors and tracer magnet volume, as well as the proximal part of the torque drive spring 655. The cylindrical mu-metal shield essentially absorbs the magnetic lines from a torque spring having been magnetized and guides them towards the circumferential shield and thereby limits the extent of the disturbing field of the torque spring in axial direction and thus towards the sensors. At the same time the cylindrical shield helps reduce the influence of external magnetic fields EMF on the sensor electronics arranged in the interior of the cylindrical volume.

Although the cylindrical mu-metal shield 1020 principally will also absorb magnetic lines from the tracer magnet 660M, this will influence the measuring performance to a smaller degree as (i) the torque drive spring 655 is axially arranged farther away from the magnetic sensors 1066M than the tracer magnet, and (ii) the torque spring is arranged radially closer to the shield than the tracer magnet. In this way the sensor system will be able to measure the magnetic field from the tracer magnet as only a smaller portion of the field is absorbed by the shield, whereas the above-described geometrical properties will allow a magnetic field from the torque spring to be absorbed by the shield to a high degree and thus influence the sensors to a smaller extent.

Figure 22:
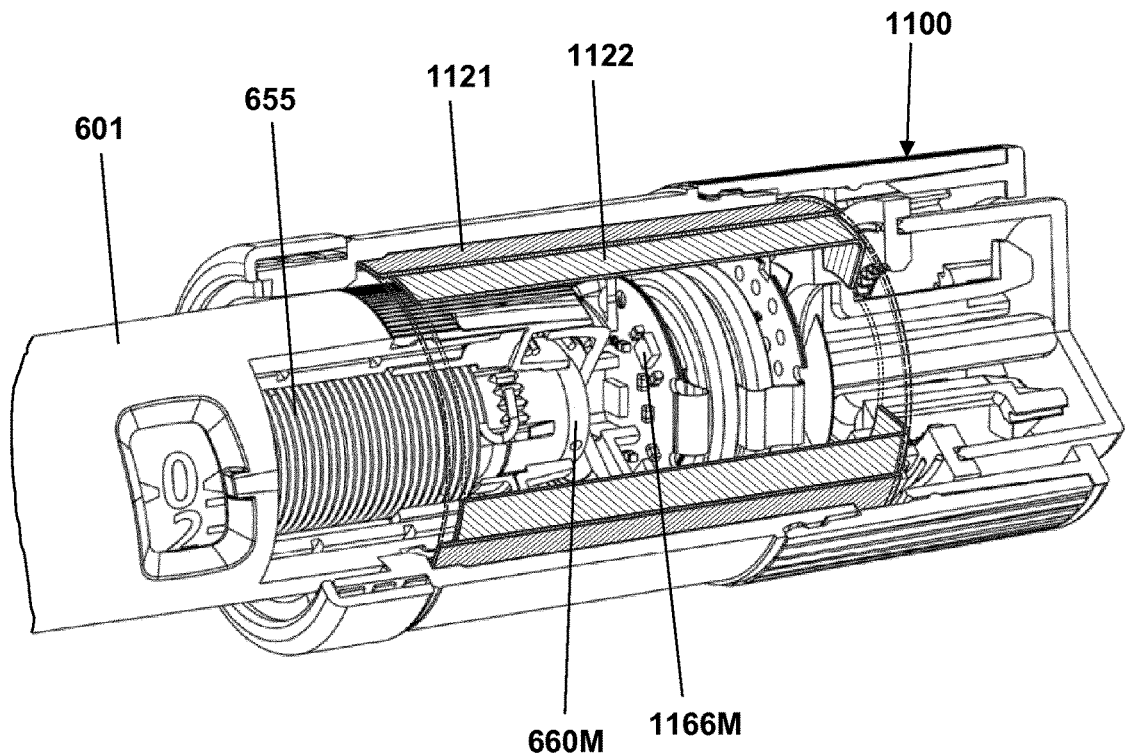
FIG. 22 shows a yet further embodiment of add-on device mounted on a drug delivery device.

FIG. 22 shows an embodiment of an add-on dose logging device 1100 in which an outer shield of steel 1121, able to handle stronger magnetic fields without saturation, is applied to provide a path for external magnetic fields. An inner shield 1122 in mu-metal is arranged to provide a path for a relative weak internal magnetic field introduced by the torque spring, without being saturated by a strong external field.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery assembly, comprising:
a housing,
a drug reservoir or structure for receiving a drug reservoir,
drug expelling structure comprising:
   a dose setting member allowing a user to set a dose amount of drug to be expelled from the drug reservoir,
   a release member actuatable between a proximal position and a distal position, the proximal position allowing a dose amount to be set, the distal position allowing the drug expelling structure to expel a set dose,
   a drive spring arranged to be strained during dose setting and released by the release member to thereby drive expelling of an amount of drug from the drug reservoir, and
   an indicator adapted to rotate corresponding to a reference axis and relative to the housing during expelling of a dose amount of drug, the amount of rotation being indicative of the size of the expelled dose amount, the indicator being moved axially between a proximal position and a distal position when the release member is moved to its distal position,
an actuatable release assembly moveable between an initial proximal position, an intermediate position in which the release member is engaged in its proximal position, and an actuated distal position in which the release member has been moved to its distal position,
a sensor system comprising:
   a sensor component adapted to measure a property of the indicator indicative of a rotational position and/or a rotational movement of the indicator, and
   a processor configured to determine on the basis of measured values from the sensor component a rotational position and/or amount of rotational movement of the indicator,
wherein the sensor component is coupled to and moves axially with the release assembly, this allowing the sensor component to move axially together with the indicator as the indicator is moved axially between its proximal position and its distal position.

2. The drug delivery assembly as in claim 1, wherein:
the indicator can be actuated to move axially between an initial indicator proximal position, an indicator intermediate position and an actuated indicator distal position, and
the indicator is adapted to start rotating when in the indicator intermediate position.

3. The drug delivery assembly as in claim 1, wherein:
the sensor system is adapted to measure a property of the indicator indicative of rotational position and/or rotational movement of the indicator during axial movement of the indicator between the indicator intermediate position and the actuated indicator distal position, the sensor component moving axially together with the indicator.

4. The drug delivery assembly as in claim 1, wherein:
a property of the indicator indicative of a first rotational position is measured with the sensor component axially positioned between the initial proximal and the intermediate position, and a property of the indicator indicative of a second rotational position is measured with the sensor component axially positioned between the intermediate and the distal position.

5. The drug delivery assembly as in claim 1, wherein:
the sensor system comprises a plurality of sensor components, and
the processor is configured to determine on the basis of measured values from the plurality of sensor components a rotational position and/or amount of rotational movement of the indicator.

6. The drug delivery assembly as in claim 1, wherein:
the sensor system comprises a switch arranged to be actuated from an off-state to an on-state when the release assembly is actuated from the initial proximal position to the intermediate position to thereby energize the sensor system to an operatable state.

7. The drug delivery assembly as in claim 6, wherein:
the switch is arranged to be actuated when the release assembly engages the release member in its proximal position.

8. The drug delivery assembly as in claim 1, wherein:
the sensor system is coupled to and moves axially with the release assembly.

9. The drug delivery assembly as in claim 1, wherein the indicator comprises a magnetic component, at least one sensor component being a magnet sensor adapted to measure one or more components of a magnetic field.

10. The drug delivery assembly as in claim 1, comprising a drug delivery device and an add-on device adapted to be releasably mounted on the drug delivery device, the drug delivery device comprising:
the housing,
the drug reservoir or the structure for receiving a drug reservoir, and
the drug expelling structure,
and the add-on device comprising:
the release assembly, and
the sensor system.

11. The drug delivery assembly as in claim 10, wherein the dose setting member is rotatable, the add-on device further comprising:
an add-on housing adapted to be releasably attached to the drug delivery device housing,
an add-on dose setting member adapted to engage, directly or indirectly, the dose setting member, and
an actuatable add-on release member coupled to the release assembly and axially moveable relative to the add-on housing between:
   (i) a proximal dose setting position in which the add-on dose setting member, with the add-on device mounted on the drug delivery device, can be operated to rotate the dose setting member to set a dose, and
   (ii) a distal dose expelling position in which the release member, with the add-on device mounted on the drug delivery device, is moved to its distal position to release a set dose.

12. An add-on device adapted to be releasably mounted on a drug delivery device, the drug delivery device comprising:
a housing,
a drug reservoir or means for receiving a drug reservoir,
drug expelling means comprising:
   a rotatable dose setting member allowing a user to set a dose amount of drug to be expelled from the drug reservoir, a release member actuatable between a proximal position and a distal position, the proximal position allowing a dose amount to be set, the distal position allowing the drug expelling means to expel a set dose, a drive spring arranged to be strained during dose setting and released by the release member to thereby drive expelling of an amount of drug from the drug reservoir, an indicator adapted to rotate corresponding to a reference axis and relative to the housing during expelling of a dose amount of drug, the amount of rotation being indicative of the size of the expelled dose amount, the indicator being moved axially between a proximal position and a distal position when the release member is moved to its distal position, wherein the indicator can be actuated to move axially between an initial indicator proximal position, an indicator intermediate position and an actuated indicator distal position, and wherein the indicator is adapted to start rotating when in the indicator intermediate position, the add-on device comprising:

an add-on housing adapted to be releasably attached to the drug delivery device housing, a sensor system comprising:
  a sensor component adapted to measure a property of the indicator indicative of a rotational position and/or a rotational movement of the indicator, and
  a processor configured to determine on the basis of measured values from the sensor component a rotational position and/or amount of rotational movement of the indicator, an add-on dose setting member adapted to engage, directly or indirectly, the dose setting member, and an actuatable release assembly moveable between an initial proximal position, an intermediate position in which the release member is engaged in its proximal position, and an actuated distal position in which the release member has been moved to its distal position, an actuatable add-on release member coupled to the release assembly and axially moveable relative to the add-on housing between:
  (i) a proximal dose setting position in which the add-on dose setting member (680, 780), with the add-on device mounted on the drug delivery device, can be operated to rotate the dose setting member to set a dose, and
  (ii) a distal dose expelling position in which the release member, with the add-on device mounted on the drug delivery device, is moved to its distal position to release a set dose, wherein:

the sensor component is coupled to and moves axially with the release assembly, this allowing the sensor component to move axially together with the indicator as the indicator is moved axially between its proximal position and its distal position.

13. A method for capturing dose related data from a drug delivery assembly, comprising the steps:

(i) providing a drug delivery assembly comprising:
drug expelling structure comprising:
  a dose setting member allowing a user to set a dose amount of drug to be expelled from the drug reservoir,
  a release member actuatable between a proximal position and a distal position, the proximal position allowing a dose amount to be set, the distal position allowing the drug expelling structure to expel a set dose,
  a drive spring arranged to be strained during dose setting and released by the release member to thereby drive expelling of an amount of drug from the drug reservoir, and
  an indicator adapted to rotate corresponding to a reference axis and relative to the housing during expelling of a dose amount of drug, the amount of rotation being indicative of the size of the expelled dose amount, the indicator being moved axially between a proximal position and a distal position when the release member is moved to its distal position,
an actuatable release assembly moveable between an initial proximal position, an intermediate position in which the release member is engaged in its proximal position, and an actuated distal position in which the release member has been moved to its distal position,
a sensor system comprising:
  a sensor component coupled to and moving axially with the release assembly, the sensor component being adapted to measure a property of the indicator indicative of a rotational position and/or a rotational movement of the indicator, and
  a processor configured to determine on the basis of measured values from the sensor component a rotational position and/or amount of rotational movement of the indicator, (ii) moving the release assembly into engagement with the release member, (iii) moving the release assembly to release the drug expelling structure to expel a set dose, and (iv) while the indicator is being moved axially by the release assembly after the drug expelling structure has been released, operate the sensor system to determine a rotational position and/or amount of rotational movement of the indicator.

* * * * *

UNITED STATES PATENT AND TRADEMARK OFFICE
CERTIFICATE OF CORRECTION

Page 1 of 1

PATENT NO. : 12,239,826 B2
APPLICATION NO. : 17/292952
DATED : March 4, 2025
INVENTOR(S) : Bom et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 877 days.

Signed and Sealed this
Sixteenth Day of September, 2025

Coke Morgan Stewart
*Acting Director of the United States Patent and Trademark Office*